US012782368B2

(12) United States Patent
Zheng et al.

(10) Patent No.: US 12,782,368 B2
(45) Date of Patent: Nov. 3, 2026

(54) CHEMILUMINESCENT ANDROSTENEDIONE CONJUGATES

(71) Applicant: Siemens Healthcare Diagnostics Inc., Tarrytown, NY (US)

(72) Inventors: Yi Feng Zheng, Wilmington, DE (US); Lauren Parker, Elkton, MA (US); John Driscoll, Bear, DE (US); Zhijian Zhao, Wilmington, DE (US); Patrick Donovan, Hopkinton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1139 days.

(21) Appl. No.: 16/488,524

(22) PCT Filed: Feb. 23, 2018

(86) PCT No.: PCT/US2018/019467

§ 371 (c)(1),
(2) Date: Aug. 23, 2019

(87) PCT Pub. No.: WO2018/156925

PCT Pub. Date: Aug. 30, 2018

(65) Prior Publication Data

US 2021/0003596 A1 Jan. 7, 2021

Related U.S. Application Data

(60) Provisional application No. 62/462,904, filed on Feb. 23, 2017.

(51) Int. Cl.

| | |
|---|---|
| ***G01N 33/74*** | (2006.01) |
| ***C07J 1/00*** | (2006.01) |
| ***C07J 43/00*** | (2006.01) |
| ***G01N 33/58*** | (2006.01) |
| *C07J 31/00* | (2006.01) |
| *C07J 41/00* | (2006.01) |
| *G01N 21/64* | (2006.01) |

(52) U.S. Cl.

CPC .......... *G01N 33/743* (2013.01); *C07J 1/0011* (2013.01); *C07J 43/003* (2013.01); *G01N 33/582* (2013.01); *C07J 31/003* (2013.01); *C07J 41/0016* (2013.01); *G01N 2021/6439* (2013.01)

(58) Field of Classification Search

CPC ............... G01N 33/582; G01N 33/743; G01N 2021/6439; C07J 1/0011; C07J 31/003; C07J 41/0016; C07J 43/003; C07J 41/0038; C07J 51/00

See application file for complete search history.

(56) References Cited

U.S. PATENT DOCUMENTS

| | | | |
|---|---|---|---|
| 5,656,426 | A | 8/1997 | Law et al. |
| 2002/0022609 | A1 | 2/2002 | Loozen et al. |
| 2003/0045716 | A1 | 3/2003 | Natrajan et al. |
| 2010/0099077 | A1 | 4/2010 | Natrajan et al. |

FOREIGN PATENT DOCUMENTS

| | | | |
|---|---|---|---|
| CN | 105153115 | | 12/2015 |
| CN | 107652344 | | 2/2018 |
| EP | 3067345 | A1 | 9/2016 |
| GB | 1451626 | | 10/1976 |
| JP | H10-503169 | | 3/1998 |
| JP | 2002534356 | | 10/2002 |
| JP | 2010-506857 | | 3/2010 |
| JP | 2013510934 | | 3/2013 |
| KR | 10-2002-0092890 | | 1/2002 |
| WO | 9527702 | | 10/1995 |
| WO | 0035950 | | 6/2000 |
| WO | 2008067055 | | 6/2008 |
| WO | 2009100327 | | 8/2009 |

OTHER PUBLICATIONS

Solo et al. (Steroids, 1982, 40(6), pp. 603-614).*
Andstead et al. (Steroids, 1997, 62, 268-303).*
PCT Search Report and Written Opinion for International Application No. PCT/US2018/019467, mailed on Apr. 9, 2018.
Lemcke Susanne et al "DHEA-Bodipy—a functional fluorescent DHEA analog for live cell imaging"; Molecular and Cellular Endocrinology vol. 314, No. 1, Jan. 15, 2010, pp. 31-40 [online].
Herbst Karen L. et al "The Male Contraceptive Regimen of Testosterone and Levonorgestrel Significantly Increases Lean Mass in Healthy Young Men in 4 Weeks, but Attenuates a Decrease in Fat Mass Induced by Testosterone Alone" The Journal of Clinical Endocrinology and Metabolism, vol. 88, No. 3, Mar. 1, 2003, pp. 1167-1173; abstract; p. 1167.
Nordblom, G. et al: "A specific radioiimmunoassay for androstenedione with reduced bridge-binding"; Steroids; Elsevier Science Publishers; New York, NY, US; vol. 44; No. 3; Sep. 1, 1984; pp. 275-282.
Nordblom, G. et al: "A chemical approach to solving bridging phenomena in steroid radioimnunoassays"; Steroids; Elsevier Science Publishers; New York, NY, US; vol. 38; No. 2; Aug. 1, 1981; pp. 161-173.
Adamczyk, M. et al: "0-(Acridinium)hydroxylamine (AHA): a reagent for the preparation or chemiluminescent acridinium oxime (AO)-steroid conjugates"; Steroids; Elsevier Science Publishers; New York, NY, US; vol. 65; No. 7; Jul. 1, 2000; pp. 387-394.
Solo, A. et al: "7a-Alkyltestosterone derivatives: Synthesis and activity as androgens and as aromatase inhibitors"; Steroids; Elsevier Science Publishers; New York, NY, US; vol. 40; No. 6; Dec. 1, 1982; pp. 603-614.
Richardson et al., Clin Chem 31.10 (1985): 1664-1668.
Kushnir, M. M.; Blamires, T.; Rockwood, A. L.; Robert, W. L.; Yue, B. F.; Erdogan, E.; Bunker, A. M.; Meikle, A. W. "Liquid Chromatography-Tandem Mass Spectrometry Assay for Androstenedione, Dehydroepiandrosterone and Testosterone with Pediatric and Adult Reference Intervals" Clin Chem, (2010), vol. 56, 1138.

(Continued)

*Primary Examiner* — Susanna Moore

(57) ABSTRACT

Chemiluminescent androstenedione conjugates are disclosed. These chemiluminescent androstenedione conjugates may be used as chemiluminescent tracers in immunoassays for the quantification and identification of certain analytes.

3 Claims, 7 Drawing Sheets

(56) References Cited

OTHER PUBLICATIONS

Haring, R.; Hannemann, A; John, U ; Radke, D.; Nauck, M.; Wallaschofski, H.; Owen, L.; Adaway, J.; Keevil, B. G., Brabant, G. "Age-Specific Reference Ranges for Serum Testosterone and Androstenedione Concentrations in Women Measured by Liquid Chromatography-Tandem Mass Spectrometry" J Clin Endocrinol Meta, (2012), vol. 97, 408.

Fanelli, F.; Belluomo, I.; Di Lallo, V. D.; Cuomo, G.; De lasio, R.; Baccini, M.; Casadio, E.; Casetta, B.; Vicennati, V.; Gambineri, A.; Grossi, G.; Pasquali, R.; Pagotto, U. "Serum Steroid Profiling by Isotopic-Dilution-Liquid Chromatography-Mass Spectrometry: Comparison with Current Immunoassays and Reference Intervals in Healthy Adults" Steroids, (2011), vol. 76, 244.

Janse, F.; Eijkemans, M. J. C. ; Goverde, A. J.; Lentjes, E. G. W. M.; Hoek, A.; Lambalk, C. B.; Hickey, T. E.; Fausner, B. C. J. M.; Norman, R. J. "Assessment of Androgen Concentration in Women: Liquid Chromatography-Tandem Mass Spectrometry and Extraction RIA Show Comparable Results" Eur J Endocrinol, (2011), vol. 165, 925.

Natrajan, A.; Sharpe, D.; Wen, D. "Zwitterionic Reagents for Labeling, Cross-Linking and Improving the Performance of Chemiluminescent Immunoassays" Org Biomol Chem 2012, vol. 10, 1883.

Natrajan, A.; Sharpe, D.; Costello, J.; Jiang, Q. P. "Enhanced Immunoassay Sensitivity Using Chemiluminescent Acridinium Esters with Increased Light Output" Ann Biochem, (2010), vol. 406, 204.

Natrajan, A.; Sharpe, D.; Wen, D. "Effect of Surfactants on the Chemiluminescence of Acridinium Dimethylphenyl Ester Labels and Their Conjugates" Org Biomol Chem, (2011), vol. 9, 5092.

* cited by examiner

CHEMILUMINESCENT ANDROSTENEDIONE CONJUGATES

This application claims the priority of U.S. Provisional Application No. 62/462,904, filed Feb. 23, 2017, which is hereby incorporated by reference in its entirety.

FIELD OF INVENTION

The present invention relates to chemiluminescent androstenedione conjugates. These chemiluminescent androstenedione conjugates are used as chemiluminescent tracers in immunoassays for the quantification and identification of specific analytes in a sample.

BACKGROUND OF INVENTION

The concentration of various androgens in circulating serum is directly related to a variety of physiological and behavioral systems. Specifically, the concentration in sera of the androgen androstenedione is frequently measured for detection of androgen-secreting tumors of ovarian and adrenal origin, evaluation of inborn errors of sex-steroid metabolism, or disorders of puberty. Elevated androstenedione levels are associated with diseases such as virilizing adrenal hyperplasia and polysystic ovarian syndrome. Moreover, the measurement of androstenedione in samples provides increased detection accuracy of disease than other androgens like 17-hydroxyprogesterone. Additionally, androstenedione is banned by the World Anti-Doping Agency and from the Olympic Games. Accordingly, the measurement of serum androgens is important in a variety of patients including adult patients, geriatric patients, pediatric endocrinological patients, and oncological patients.

The structure of the endogenous 4-androstenedione ("A4") hormone is illustrated below with each of its 19 carbons labeled.

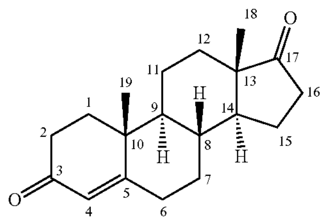

Other androstenediones include the prohormones 5-androestenedione and 1-androstenedione, which are also included on the World Anti-Doping Agency's list of prohibited substances. It will be understood that reference to androstenedione includes androstenediones including A4, 5-androstenedione and 1-androstenedione.

Various techniques have been developed for the detection of androstenedione concentration in samples. The analytical methods may use mass-spectrometry (MS) in conjunction with gas chromatography (GC) or liquid chromatography (LC). For example, a liquid chromatographic-tandem mass spectroscopic ("LC-MS/MS") assay for androstenedione and other steroids is described in Kushnir, M., et al., *Clin. Chem.* 56, 1138 (2010), hereby incorporated by reference in its entirety. However, due to the expensive equipment and longer run times required for these methods, their utility for measurements of multiples samples is limited. Androstenedione concentrations have also been measured with immunoassays which provide a cost effective, simplistic and rapid alternative to MS based analyses. These assays, like IMMULITE 2000 Androstenedione Assay or other enzyme-linked immunosorbent assays ("ELISA"), operate in a competitive binding format where the androstenedione in the sample to be measured competes with enzyme conjugated androstenedione for binding onto a limited number of antibodies. Typically, the androstenedione is conjugated to alkaline phosphatase or horseradish peroxidase. After formation of a binding complex to a solid phase comprising a limited number of sites capable of conjugation to either androstenedione or the enzyme linked androstenedione, the binding complex may be separated and undergo giving a measureable change (e.g., color). Once the solid phase is removed and the measurable change is observed, the concentration of androstenedione in the sample can be inferred. However, as shown in Fanelli, F., et al., *Steroids* 76, 244 (2011), hereby incorporated by reference in its entirety, comparisons of LC-MS/MS assays to ELISA assays indicate that androstenedione concentrations measured by ELISA methods result in a nearly 2.5 fold increase in the measured androstenedione concentrations as compared to LC-MS/MS. Such overestimation has been attributed to miscalibration and cross-reactivity of the enzyme linked androstenedione conjugates used in the immunoassay resulting in low sensitivity and accuracy for the ELISA assay.

There is a continuing need in the art for improved androstenedione immunoassays. It is therefore an object of the invention to provide chemiluminescent compounds conjugated to androstenedione capable of being used in immunoassays which provide accurate and precise measurements of the concentration of androstenedione in a sample.

SUMMARY

It has been found that chemiluminescent acridinium compounds may be conjugated to androstenedione to provide more accurate results in an immunoassay than ELISA measurements. Detectable conjugates and methods of using detectable conjugates of androstenedione are provided herein.

In one aspect of the invention, detectable conjugate of androstenedione is provided comprising an androstenedione moiety conjugated to a chemiluminescent moiety having the structure:

$$A\text{-}L\text{-}\psi \qquad (I)$$

wherein A is androstenedione (e.g. A4, 5-androstenedione, 1-androstenedione, etc.);

L is a linker; and $\psi$ is a chemiluminescent moiety comprising acridinium. In some embodiments, $\psi$ may be a acridinium ester or acridinium sulfonamide. In some embodiments, A is a monovalent androstenedione radical. In preferred embodiments, A may be a radical of 4-androstenedione ("A4"). In most embodiments, A, L, and $\psi$ are covalently bonded to one another.

In most embodiments, L has the structure $-L^C-(Z^L)_z$— where

"z" is 0 or 1;

$L^C$ is a divalent $C_{1-35}$ alkyl, alkenyl, alkynyl, aryl, or arylalkyl radical, optionally substituted with 1 to 20 heteroatoms; and $Z^L$ is a zwitterionic linker group having the structure:

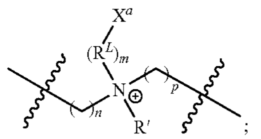

"m" is 0 (i.e. it is a bond) or 1;

"n" and "p" are independently at each occurrence an integer from 0 (i.e. it is a bond) to 10;

$X^a$ is an anionic group;

$R^L$ is a $C_{1-20}$ bivalent hydrocarbon radical (e.g., alkyl, alkenyl, aryl, alkynyl, arylalkyl, etc.), optionally substituted with 1-10 heteroatoms (e.g., N, O, S, Cl, F, Br, etc.); and R' is hydrogen or a $C_{1-10}$ alkyl.

Typically, ψ has the structure of formula (II):

(II)

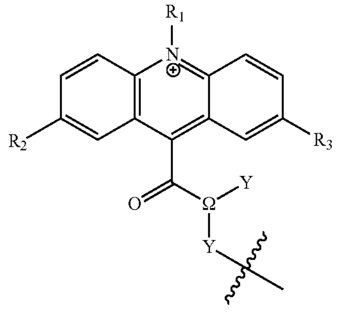

wherein Ω is CH, O, or N;

Y is selected from —R or —$R^L$—Z, or in the case where Ω is O then Y is absent;

Y' is either absent (i.e. it is a bond), or is selected from -$L_1$-, —$R^L$—, —$R^L$-$L_1$-, -$L_1$-$L_1$-, -$L_1$-$R^L$—, -$L_1$-$R^L$-$L_1$, or —$R^L$-$L_1$-$R^L$—; and Y' comprises one or more linkages to $L^C$ or $Z^L$;

$R_1$ is hydrogen, —R, —X, —$R^L$—X, -$L_1$-R, -$L_1$-X, —Z, —$R^L$—Z, -$L_1$-Z, or —$R^L$-$L_1$-$R^L$—Z;

$R_2$ and $R_3$ are independently selected from hydrogen, —R, an electron donating group, or —Z;

Z is a zwitterionic group having the structure:

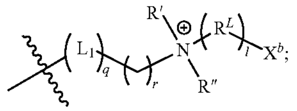

where "q" and "l" are independently 0 or 1;

"r" is independently an integer from 0 to 10;

$L_1$ is independently at each occurrence —O—, —S—, —NH—, —N($R^N$)—, —$(CH_2)_{1-10}$—, —S(=O)$_{1-2}$—, —C≡C—, —C≡C—$(CH_2)_{1-3}$—, —C(O)—, —O—C(O)—, —C(O)—$(CH_2)_{1-4}$—, —$(CH_2)_{1-4}$—C(O)—, —C(O)—O—, —C(O)—N($R^N$)—, —C(O)—NH—, —N($R^N$)—C(O)—, —NH—C(O)—, —C(O)—N($R^N$)—$(CH_2)_{1-3}$—, —$(CH_2)_{1-3}$—C(O)—N($R^N$)—, —NH—S(O)$_{1-2}$—, —N($R^N$)—S(O)$_{1-2}$—, —S(O)$_{1-2}$—N($R^N$)—, —S(O)$_{1-2}$—NH—, —$(CH_2)_{1-3}$—NH—S(O)$_{1-2}$—, —$(CH_2)_{1-3}$—N($R^N$)—S(O)$_{1-2}$—, —$(CH_2)_{1-3}$—S(O)$_{1-2}$—N($R^N$)—, —$(CH_2)_{1-3}$—S(O)$_{1-2}$—NH—, —O—$(CH_2)_{1-4}$—, —$(CH_2)_{1-4}$—O—, —S—$(CH_2)_{1-4}$—, —$(CH_2)_{1-4}$—S—, —NH—$(CH_2)_{1-4}$—, —N($R^N$)—$(CH_2)_{1-4}$—, —$(CH_2)_{1-4}$—N($R^N$)—, —$(OCH_2)_{1-10}$—, —$(CH_2O)_{1-10}$—, —$(OCH_2CH_2)_{1-10}$—, or —$(CH_2CH_2O)_{1-10}$—;

$R^L$ is independently at each occurrence a $C_{1-20}$ bivalent hydrocarbon radical (e.g., alkyl, alkenyl, aryl, phenyl, mono alkyl substituted phenyl, di alkyl substituted phenyl, alkynyl, arylalkyl, etc.), optionally substituted with 1-10 heteroatoms;

R is independently at each occurrence hydrogen or $C_{1-35}$ hydrocarbon (e.g., alkyl, alkenyl, alkynyl, or aralkyl) radical, optionally substituted with 1-20 heteroatoms;

R' and R" are independently at each occurrence hydrogen or a $C_{1-10}$ alkyl;

$X^b$ is independently at each occurrence an anionic group; and $R^N$ is independently selected at each occurrence from hydrogen, or $C_{1-5}$ alkyl (e.g., methyl, ethyl, propyl, etc.).

In another aspect of the invention, a reagent is provided for the detection of an analyte comprising a detectable conjugate of androstenedione bound to a chemiluminescent acridinium. The detectable conjugate may comprise one or more (e.g., one, two, etc.) zwitterionic functional The reagent may comprise a concentration of detectable conjugate of from 10 to 30 ng/mL.

In a further aspect of the invention, an assay for the detection or quantification of an analyte in a sample is provided comprising:

(a) providing a detectable conjugate having the structure of formula (I);

(b) providing a solid support having immobilized thereon an molecule capable of forming a binding complex with said analyte and capable of forming a binding complex with said detectable conjugate;

(c) mixing said compound, said solid support, and said sample;

(d) separating said solid support from said mixture;

(e) triggering chemiluminescence of any acridinium label complexed to said solid phase;

(f) measuring the amount of light emission with a luminometer; and (g) detecting the presence or calculating the concentration of said analyte by comparing the amount of light emitted with a standard dose response curve which relates the amount of light emitted to a known concentration of the analyte.

In some embodiments, the compound is provided in a reagent which further comprises a buffer. Typically the analyte detected or quantified is androstenedione (e.g., 4-androstenedione, etc.). In some embodiments, the sample is serum.

These and other aspects of the invention will be better understood by reference to the following detailed description including the appended claims.

DETAILED DESCRIPTION

Figure 1:
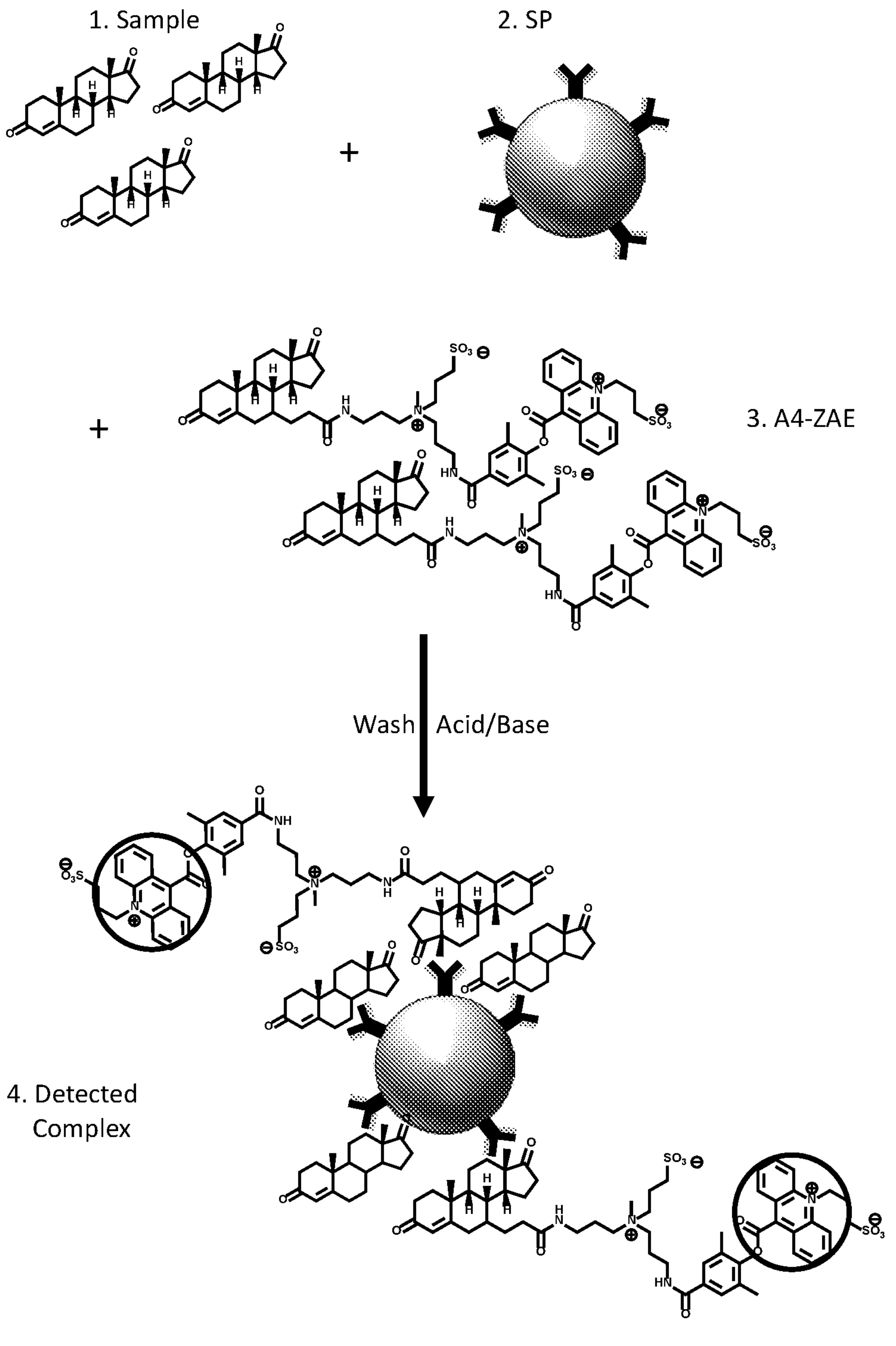
FIG. 1 illustrates an example of a competitive androstenedione immunoassay using chemiluminescent androstenedione conjugates. A sample with unknown androstenedione concentration ("1") is mixed with a reagent comprising chemiluminescent androstenedione conjugates ("2," here as androstenedione-zwitterionic acridinium ester ("A4-ZAE") conjugates) and allowed to interact with a solid phase ("3," "SP"). The solid phase has antibodies capable of forming a binding complex coated thereon. Each antibody is capable of forming a binding complex with either androstenedione from the sample or the A4-ZAE conjugates. After binding complexes have been formed, the solid phase is removed from the sample and washed. Through the use of chemiluminescence triggering agents (here acid/base), the chemiluminescent light output from the solid phase complexed with both A4 and A4 conjugates is measured. The intensity of light output is correlated with the number of chemiluminescent moieties (circled). Accordingly, the amount of androstenedione in the sample can be inferred by the amount of light output.

For convenience, certain terms employed in the specification, including the examples and appended claims, are collected here. Unless defined otherwise, all technical and scientific terms used herein have the same meaning as commonly understood by one of ordinary skill in the art to which this disclosure pertains.

Unless otherwise explicitly defined, the following terms and phrases are intended to have the following meanings throughout this disclosure:

All percentages given herein refer to the weight percentages of a particular component relative to the entire composition, including the carrier, unless otherwise indicated. It will be understood that the sum of all weight % of individual components within a composition will not exceed 100%.

The terms "a" or "an," as used in herein means one or more. As used herein, the term "consisting essentially of" is intended to limit the invention to the specified materials or steps and those that do not materially affect the basic and novel characteristics of the claimed invention, as understood from a reading of this specification.

The following definitions of various groups or substituents are used, unless otherwise described. Specific and general values listed below for radicals, substituents, and ranges, are for illustration only; they do not exclude other defined values or other values within defined ranges for the radicals and substituents. Unless otherwise indicated, alkyl, alkenyl, alkynyl, alkoxy, and the like denote straight, branched, and cyclic groups, as well as any combination thereof.

The term "hydrocarbon" refers to a radical or group containing carbon and hydrogen atoms. Examples of hydrocarbon radicals include, without limitation, alkyl, alkenyl, alkynyl, aryl, aryl-alkyl, alkyl-aryl, and any combination thereof (e.g., alkyl-aryl-alkyl, etc.). As used herein, unless otherwise indicated, hydrocarbons may be monovalent or multivalent (e.g., divalent, trivalent, etc) hydrocarbon radicals. A radical of the form $-(CH_2)_n-$, including a methylene radical, i.e., $-CH_2-$, is regarded as an alkyl radical if it does not have unsaturated bonds between carbon atoms. Unless otherwise specified, all hydrocarbon radicals (including substituted and unsubstituted alkyl, alkenyl, alkynyl, aryl, aryl-alkyl, alkyl-aryl, etc.) may have from 1-35 carbon atoms. In other embodiments, hydrocarbons will have from 1-20 or from 1-12 or from 1-8 or from 1-6 or from 1-3 carbon atoms, including for example, embodiments having one, two, three, four, five, six, seven, eight, nine, or ten carbon atoms. Hydrocarbons may have from about 2 to about 70 atoms or from 4 to about 40 atoms or from 4 to about 20 atoms.

A "substituted" hydrocarbon may have as a substituent one or more hydrocarbon radicals, substituted hydrocarbon radicals, or may comprise one or more heteroatoms. Any hydrocarbon substituents disclosed herein may optionally include from 1-20 (e.g., 1-10, 1-5, etc.) heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In preferred embodiments, the heteroatoms may be selected from O, N, or S. In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo").

In addition, the phrase "substituted with a[n]" as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Unless otherwise specified, any compound disclosed herein which has one or more chiral centers may be in the form of a racemic mixture with respect to each chiral center, or may exist as pure or substantially pure (e.g., great than about 98% ee) R or S enantiomers with respect to each chiral center, or may exist as mixtures of R and S enantiomers with respect to each chiral center, wherein the mixture comprises an enantiomeric excess of one or the other configurations, for example an enantiomeric excess (of R or S) of more than 60% or more than 70% or more than 80% or more than 90%, or more than 95%, or more than 98%, or more than 99% enantiomeric excess. In some embodiments, any chiral center may be in the "S" or "R" configurations. In preferred embodiments the chiral center which the androstenedione is conjugated through may be in a single configuration. In preferred embodiments, the indicated carbon position (e.g., carbon 3, 6, 7, 17, 19, etc.) is conjugated through only the a (e.g., A(3α), A(6α), A(7α), A(17α), A(19α), etc.) or β (e.g., A(3β), A(6β), A(7β), A(17α), A(19α), etc.) orientation.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

In general, and unless otherwise indicated, substituent (radical) prefix names are derived from the parent hydride by either (i) replacing the "ane" or in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Radicals of steroids may also be designated with the "yl," "diyl," "triyl," "tetrayl," etc. suffixes. Accepted contracted named of steroids include androstenedionyl, 4-androstenedionyl, androstendion-7-yl, etc. Conventional numbering/lettering systems are also adhered to for substituent numbering and the nomenclature of fused, spiro, bicyclic, tricyclic, polycyclic rings.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substituents. Examples of alkyl groups include without limitation methyl, ethyl, n-propyl, isopropyl, and tent-butyl. Any alkyl group referenced herein (e.g., R, R', R", $R_1$, $R_2$, $R_3$, $R_4$, $R_5$, etc.) may have from 1-35 carbon atoms. In other embodiments, alkyl groups will have from 1-20 or from 1-12 or from 1-8 or from 1-6 or from 1-3 carbon atoms, including for example, embodiments having one, two, three, four, five, six, seven, eight, nine, or ten carbon atoms.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14, etc.) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—$OCH_3$), ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). Finally, the terms "haloalkoxy" and "halothioalkoxy" refer to —O(haloalkyl) and —S(haloalkyl), respectively. The term "sulfhydryl" refers to —SH. As used herein, the term "hydroxyl," employed alone or in combination with other terms, refers to a group of formula —OH. Any alkoxy, thioalkoxy, or haloalkoxy group referenced herein (e.g., R, R', R", $R_1$, $R_2$, $R_3$, $R_4$, $R_5$, etc.) may have from 1-35 carbon atoms. In other embodiments, alkoxy, thioalkoxy, or haloalkoxy groups will have from 1-20 or from 1-12 or from 1-8 or from 1-6 or from 1-3 carbon atoms, including for example, embodiments having one, two, three, four, five, six, seven, eight, nine, or ten carbon atoms.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted, e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent. Any alkenyl group referenced herein (e.g., R, R', R", $R_1$, $R_2$, $R_3$, $R_4$, $R_5$, etc.) may have from 1-35 carbon atoms. In other embodiments, alkenyl groups will have from 1-20 or from 1-12 or from 1-8 or from 1-6 or from 1-3 carbon atoms, including for example, embodiments having one, two, three, four, five, six, seven, eight, nine, or ten carbon atoms.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated, partially saturated, or aromatic monocyclic, bicyclic, tricyclic, or other polycyclic ring system having one or more constituent heteroatom ring atoms independently selected from O, N (it is understood that one or two additional groups (e.g., $R^N$) may be present to complete the nitrogen valence and/or form a salt), or S. The heteroatom or ring carbon can be the point of attachment of the heterocyclyl substituent to another moiety. Any atom can be optionally substituted, e.g., with one or more substituents (e.g. heteroatoms or groups X). Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected R" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted, e.g., by one or more substituents. Cycloalkenyl moieties can include, e.g., cyclohexenyl, cyclohexadienyl, or norbornenyl.

As used herein, the term "cycloalkylene" refers to a divalent monocyclic cycloalkyl group having the indicated number of ring atoms.

As used herein, the term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S in the ring. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

In general, when a definition for a particular variable includes both hydrogen and non-hydrogen (halo, alkyl, aryl, etc.) possibilities, the term "substituent(s) other than hydrogen" refers collectively to the non-hydrogen possibilities for that particular variable.

In general, the limits (end points) of any range recited herein are within the scope of the invention and should be understood to be disclosed embodiments. Additionally, any half integral value within that range is also contemplated. For example, a range of about 0 to 4 expressly discloses 0, 0.5, 1, 1.5, 2, 2.5, 3, 3.5, 4, and any subset within that range (e.g., from about 1 to 2.5).

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo (e.g. F), $C_{1-12}$ straight chain or branched chain alkyl, $C_{2-12}$ alkenyl, $C_{2-12}$ alkynyl, $C_{3-12}$ cycloalkyl, $C_{6-12}$ aryl, C3-12 heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, C3-12 heteroaryl, or $C_{4-24}$ heteroarylalkyl. Unless otherwise noted, all groups described herein optionally contain one or more common substituents, to the extent permitted by valency. Further, as used herein, the phrase "optionally substituted" means unsubstituted (e.g., substituted with an H) or substituted. As used herein, the term "substituted" means that a hydrogen and/or carbon atom is removed and replaced by a substituent (e.g., a common substituent). The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

By "conjugated through" with reference to a specified carbon indicates that a linkage to the specified carbon is formed wherein an atom from linker group L is covalently bound to the specified carbon. In some embodiments, the bond between Carbon 17 or Carbon 3 of androstenedione and the linker will comprise a double bond such as an oxime or an imine in either geometric configuration.

By "stability" of chemiluminescent compounds, it is meant a minimal loss of chemiluminescent activity as measured by the loss of relative light units ("RLU") when the compounds or conjugates are stored in an aqueous solution typically, in the pH range of 6-9, which is within the physiological pH. An increased "instability" of a chemiluminescent compound as compared to another compound will have a greater loss of chemiluminescent activity.

The main objective of this invention is to disclose detectable labels of androstenedione. These compounds may be used in an immunoassay for the identification or the quantification of an analyte. The compounds of the invention may have the structure of formula (I)

$$\text{A-L-}\psi \qquad (I)$$

wherein A is an androstenedione moiety, "L" is a linking moiety and ψ is a chemiluminescent moiety. In some embodiments, the androstenedione compound (A) is androstenedione in an underivatized form except for the covalent attachment to the linker L. It is contemplated that this attachment allows for improved detection of the corresponding androstenedione analyte in a sample. Typically, the analyte is 4-androstenedione.

In some embodiments, ψ is a chemiluminescent acridinium having the structure:

(II)

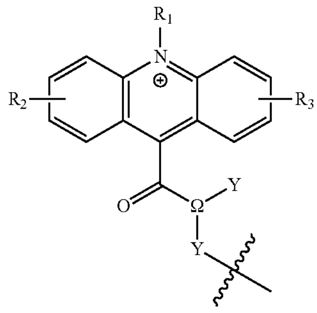

wherein Ω is CH, O, or N;

Y is selected from —R or —$R^L$—Z, or in the case where Ω is O then Y is absent;

Y' is either absent (i.e. it is a bond), or is selected from -$L_1$-, —$R^L$—, —$R^L$-$L_1$-, -$L_1$-$L_1$-, -$L_1$-$R^L$—, -$L_1$-$R^L$-$L_1$, or —$R^L$-$L_1$-$R^L$—; and Y' comprises one or more linkages to $L^C$ or $Z^L$;

$R_1$ is hydrogen, —R, —X, —$R^L$—X, -$L_1$-R, -$L_1$-X, —Z, —$R^L$—Z, -$L_1$-Z, or —$R^L$-$L_1$-$R^L$—Z;

$R_2$ and $R_3$ are independently selected from hydrogen, —R, an electron donating group, or —Z;

Z is a zwitterionic group having the structure:

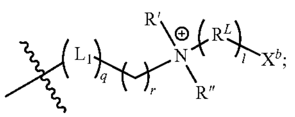

where "q" and "l" are independently 0 or 1;

"r" is independently an integer from 0 to 10;

$L_1$ is independently at each occurrence —O—, —S—, —NH—, —N($R^N$)—, —$(CH_2)_{1-10}$—, —S(=O)$_{1-2}$—, —C=C—, —C=C—$(CH_2)_{1-3}$—, —C(O)—, —O—C(O)—, —C(O)—$(CH_2)_{1-4}$—, —$(CH_2)_{1-4}$—C(O)—, —C(O)—O—, —C(O)—N($R^N$)—, —C(O)—NH—, —N($R^N$)—C(O)—, —NH—C(O)—, —C(O)—N($R^N$)—$(CH_2)_{1-3}$—, —$(CH_2)_{1-3}$—C(O)—N($R^N$)—, —NH—S(O)$_{1-2}$—, —N($R^N$)—S(O)$_{1-2}$—, —S(O)$_{1-2}$—N($R^N$)—, —S(O)$_{1-2}$—NH—, —$(CH_2)_{1-3}$—NH—S(O)$_{1-2}$—, —$(CH_2)_{1-3}$—N($R^N$)—S(O)$_{1-2}$—, —$(CH_2)_{1-3}$—S(O)$_{1-2}$—N($R^N$)—, —$(CH_2)_{1-3}$—S(O)$_{1-2}$—NH—, —O—$(CH_2)_{1-4}$—, —$(CH_2)_{1-4}$—O—, —S—$(CH_2)_{1-4}$—, —$(CH_2)_{1-4}$—S—, —NH—$(CH_2)_{1-4}$—, —N($R^N$)—$(CH_2)_{1-4}$—, —$(CH_2)_{1-4}$—N($R^N$)—, —$(OCH_2)_{1-10}$—, —$(CH_2O)_{1-10}$—, —$(OCH_2CH_2)_{1-10}$—, or —$(CH_2CH_2O)_{1-10}$—;

$R^L$ is independently at each occurrence a $C_{1-20}$ bivalent hydrocarbon radical (e.g., alkyl, alkenyl, aryl, phenyl, mono alkyl substituted phenyl, di alkyl substituted phenyl, alkynyl, arylalkyl, etc.), optionally substituted with 1-10 heteroatoms;

R is independently at each occurrence hydrogen or $C_{1-35}$ hydrocarbon (e.g., alkyl, alkenyl, alkynyl, or aralkyl) radical, optionally substituted with 1-20 heteroatoms;

R' and R" are independently at each occurrence hydrogen or a $C_{1-10}$ alkyl;

$X^b$ is independently at each occurrence an anionic group; and $R^N$ is independently selected at each occurrence from hydrogen, or $C_{1-5}$ alkyl (e.g., methyl, ethyl, propyl, etc.). Typically, L has the structure -$L^C$-$(Z^L)_z$— where "z" is 0 or 1;

$L^C$ is a divalent $C_{1-35}$ alkyl, alkenyl, alkynyl, aryl, or arylalkyl radical, optionally substituted with 1 to 20 heteroatoms; and $Z^L$ is a zwitterionic linker group having the structure:

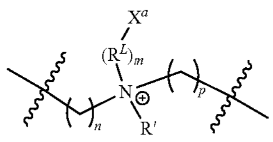

"m" is 0 (i.e. it is a bond) or 1;

"n" and "p" are independently at each occurrence an integer from 0 (i.e. it is a bond) to 10;

$X^a$ is an anionic group;

$R^L$ is a $C_{1-20}$ bivalent hydrocarbon radical (e.g., alkyl, alkenyl, aryl, alkynyl, arylalkyl, etc.), optionally substituted with 1-10 heteroatoms; and R' is hydrogen or a $C_{1-10}$ alkyl.

In preferred embodiments, ψ has the structure of formula (IIa)

(IIa)

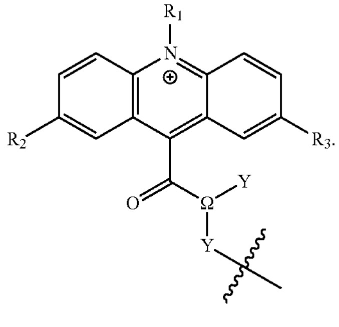

Generally, the anionic group ($X^a$ and/or $X^b$) may provide an anionic charge to counterbalance any cationic charge directly or indirectly covalently attached and in order to form a zwitterion. In some embodiments, $X^a$ and $X^b$ are independently at each occurrence carboxylate (—C(O)$O^-$), sulfonate (—$SO_3^-$), sulfate (—$OSO_3^-$), phosphate (—OP(O)($OR^P$)$O^-$), or oxide (—$O^-$), and $R^P$ is hydrogen or $C_{1-12}$ hydrocarbon optionally substituted with up to 10 heteroatoms.

The $R_1$ group attached to the positively charged nitrogen of the acridinium nucleus is optionally substituted with up to 20 heteroatoms (e.g., N, O, S, P, Cl, Br, F, etc.) and therefore may in combination with the positively charged acridinium nitrogen atom, constitute a zwitterionic group. For example a sulfopropyl or sulfobutyl group attached to the acridinium nitrogen may form a zwitterionic pair. The $R_1$ group may also be neutral (e.g., methyl) or by itself be zwitterionic (e.g., $R_1$ is —Z, —$R^L$—Z, -$L_8$-Z, or —$R^L$-$L_8$-$R^M$—Z). In some embodiments, $R_1$ has the structure:

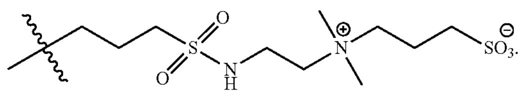

When the compound is charged (e.g., $R_1$ has a net neutral charge, etc.), the compound may optionally include a counterion to balance the positively charged nitrogen of the acridinium nucleus. While there is essentially no limitation on the selection of the counterion, in some embodiments the counterion is selected from $CH_3SO_4^-$, $FSO_3^-$, $CF_3SO4^-$, $C_4F_9SO_4^-$, $CH_3C_6H_4SO_3^-$, halide (e.g., $Cl^-$, $F^-$, $Br^-$, etc.), $CF_3COO^-$, $CH_3COO^-$, or $NO_3^-$. In some embodiments, $R_1$ is methyl, ethyl, propyl, or isopropyl. In other embodiments, $R_1$ comprises —$R^L$—X and —X is sulfonate (—$SO_3^-$). In some embodiments, $R_1$ is —$R^L$—X and —X is sulfonate (—$SO_3^-$). In some embodiments, $R_1$ is —$R^L$—X or -$L_8$-Z. In some embodiments, $L_8$ is —$S(O)_2$—NH— or —$(CH_2)_{1-3}$—$S(O)_2$—NH—. $R_1$ may comprise a sulfopropyl group (—$(CH_2)_3$—$SO_3^-$). In preferred embodiment, $R_1$ is sulfopropyl.

The nature of the chemiluminescent acridinium is not particularly restricted and included chemiluminescent acridinium esters and sulfonamides without limitation. In preferred implementations, the chemiluminescent acridinium ψ is an acridinium ester. For example, ψ may have the structure:

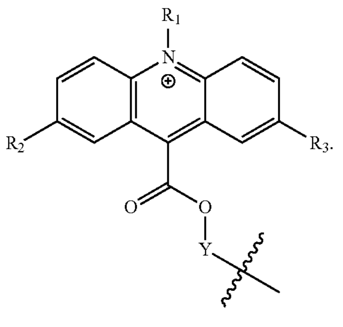

In preferred embodiments, ψ has the structure of formula (IIb):

(IIb)

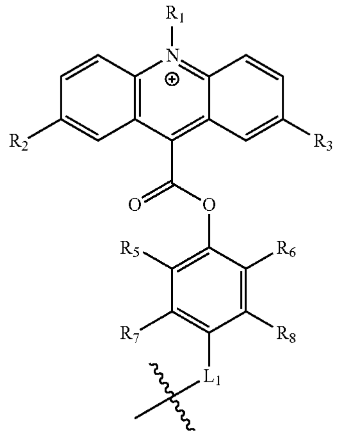

wherein $R_5$-$R_7$ are independently hydrogen or $C_{1-35}$ alkyl, alkenyl, alkynyl, aryl, alkoxy, alkylthio, or amino; and wherein $L_1$ is covalently bonded to L (e.g., to $L^C$ or $Z^L$). In some embodiments, $L_1$ in formula (IIa) is —C(O)—NH—. In some embodiments, $R_5$ and $R_6$ are each methyl and $R_7$ and $R_8$ are each hydrogen.

A person of ordinary sill would recognize that the substituents on the chemiluminescent acridinium ester may be modified to vary the rate and yield of light emission, to reduce the non-specific binding, increase stability, or increase hydrophilicity, but what is important for the present invention is that the chemiluminescent acridinium ester not interfere substantially with the binding of the androstenedione compound (A) with an antibody, and specifically for the corresponding unconjugated androstenedione compound. Examples of substituent variability are disclosed in Natrajan et al. in U.S. Pat. No. 7,309,615, hereby incorporated by reference herein, which describes high quantum yield acridinium compounds containing alkoxy groups (OR*) at C2 and/or C7, wherein R* is a group comprising a sulfopropyl moiety or ethylene glycol moieties or combinations thereof. In some embodiments, $R_2$ and/or $R_3$ may be alkoxy groups (e.g., OR and/or OR*.). Natrajan et al. in International Pub. No. WO2015/006174, hereby incorporated by reference in its entirety, also describes hydrophilic high quantum yield, chemiluminescent acridinium esters possessing certain electron-donating functional groups at the C2 and/or C7 positions as well. These electron donating groups at $R_1$ and/or $R_2$ may have the structure:

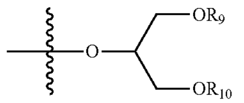

or

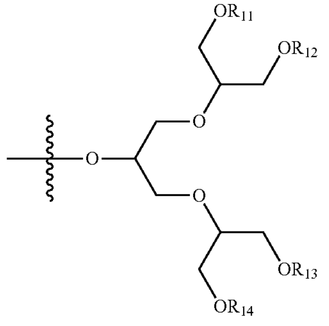

wherein $R_9$-$R_{14}$ are independently selected at each occurrence a methyl group or a group —$(CH_2CH_2O)_aCH_3$, where a is an integer from 1 to 5. In some embodiments, $R_2$ and $R_3$ are independently at each occurrence hydrogen, alkyl (e.g., methyl, ethyl, propyl, isopropyl, etc.), or alkoxy (e.g., methoxy, ethoxy, propoxy, or isopropoxy, etc.). In some embodiments, $R_2$ and $R_3$ are each hydrogen. In other embodiments, $R_2$ or $R_3$ is hydrogen and the other of $R_2$ or $R_3$ is alkoxy or an electron donating group.

The detectable conjugate may comprise a chemiluminescent acridinium sulfonamide. For example, ψ may have the structure of formula (IIc):

(IIc)

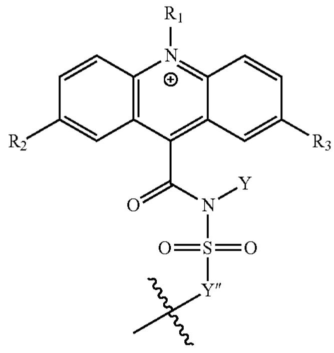

wherein Y" is either absent or is -$L_1$-, —$R^L$—, or —$R^L$-$L_1$-, where Y" is covalently attached to L (e.g., to $L^C$ or $Z^L$).

In some embodiments, $R^L$ is an optionally substituted five- or six-membered bivalent aromatic hydrocarbon. For example, any $R^L$ may have the structure:

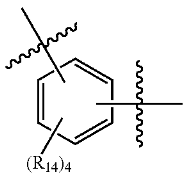

wherein $R_{14}$ is independently at each occurrence hydrogen, halogen, or R. In some embodiments, $R^L$ has the structure:

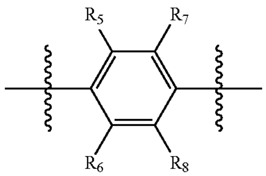

wherein $R_5$-$R_7$ are independently $C_{1-35}$ alkyl, alkenyl, alkynyl, aryl, alkoxy, alkylthio, or amino. In some embodiments, $R_7$ and $R_8$ are each hydrogen and $R_5$ and $R_6$ are each methyl. In some embodiments, ψ comprises two flanking methyl groups on a phenolic ester to stabilize the bond as disclosed in Law et al. *Journal of Bioluminescence and Chemiluminescence* 4: 88-89 (1989), hereby incorporated by reference in its entirety. In some embodiments ψ has the structure:

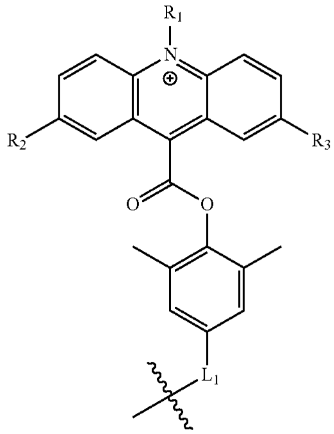

or

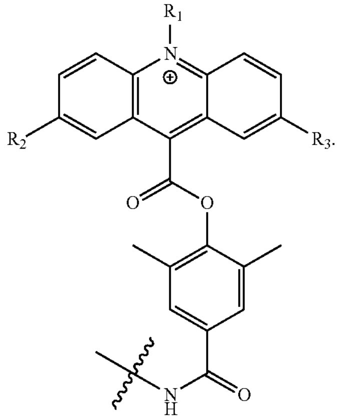

In some embodiments, A, L and ψ are each covalently linked. Portions of the covalent linkage between A and ψ may be formed from a reactive functional group for forming covalent linkages with a peptide, a protein, or a macromolecule, wherein the functional group comprises an electrophilic group, nucleophilic group, or a photoreactive group. The reactive functional group may an amine-reactive group, a thiol-reactive group, a carboxy-reactive group, a maleimidyl-reactive group, or a carbohydrate-reactive group. For example, the linkage may be formed from a reactive group selected from:

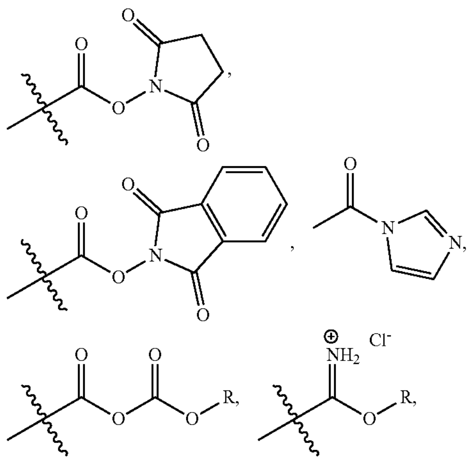

-continued

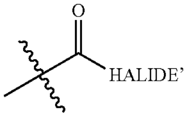

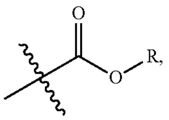

, —NCS,

—NCO,

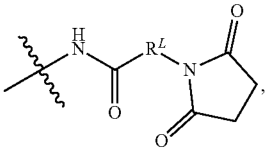

,

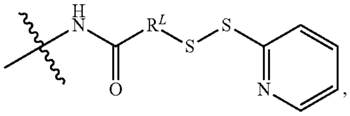

,

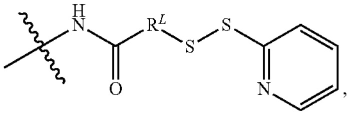

, —$SO_2Cl$,

—$N_3$, —$N_2^+Cl^-$,

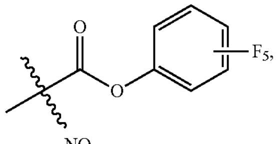

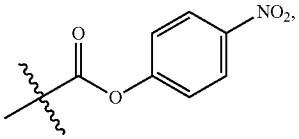

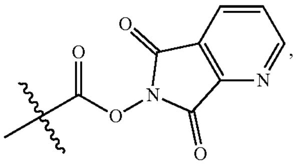

,

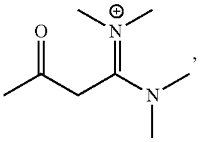

,

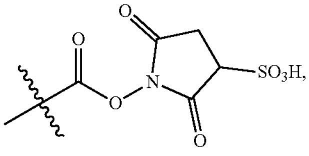

—Cl, —Br, —I, or —COOH. In some embodiments, the compound comprises a linker group having the structure —NH—C(O)— or —C(O)—NH—. In a preferred embodiment, the compound (e.g., $L^C$, ψ, etc.) comprises at least one —NH—C(O)— or —C(O)—NH— linker group.

The covalent linkage between A and ψ (e.g., L) may comprise a divalent $C_{1-20}$ alkyl, alkenyl, alkynyl, aryl, or arylalkyl radical, optionally substituted with up to 20 heteroatoms (e.g., N, O, S, P, Cl, F, Br, etc.). In some embodiments L comprises a zwitterionic linker. L may have the structure -$L^C$-$(Z^L)_z$—, wherein z is 0 or 1. $L^C$ may have the structure $$—(X_1)_{0-1}—(R^L)_{0-5}—(X_2)_{0-1}—(R^L)_{0-5}—(X_3)_{0-1}—(R^L)_{0-5}—(X_4)_{0-1}—(R^L)_{0-5}—$$

wherein $X_1$ is selected from =N—, —O—, —S—, or —$NR^N$—;

$X_2$-$X_4$ are independently selected from —O—, —S—, —$NR^N$—, —C(O)—, —$NR^N$—C(O)—, —C(O)—$NR^N$—, —O—C(O)—, or —C(O)—O—, —S—C(O)—, or —C(O)—S—; and $R^L$ is independently selected at each occurrence from —$CH_2$—, —$(CH_2CH_2O)$—, or —$(OCH_2CH_2)$—;

with the proviso that $L^C$ comprises at least one atom (or at least two atoms) in the chain between A and ψ (or between A and $Z^L$).

In some embodiments, L and/or ψ comprises —C(O)—NH—. In some embodiments, $L^C$ has the structure:

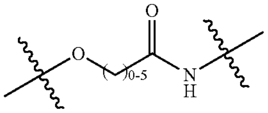

,

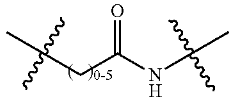

,

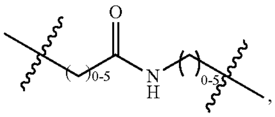

,

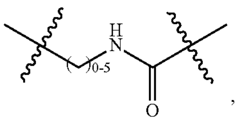

,

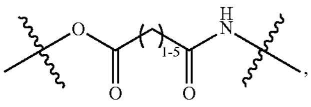

,

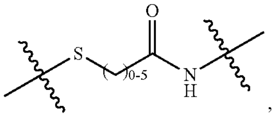

,

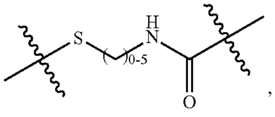

,

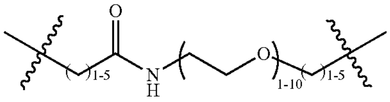

,

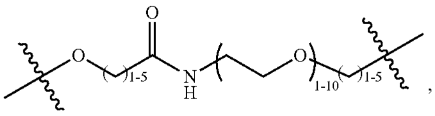

,

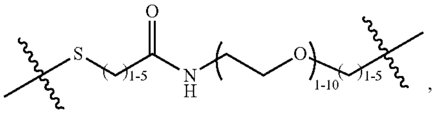

,

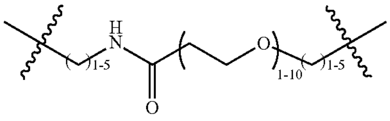

,

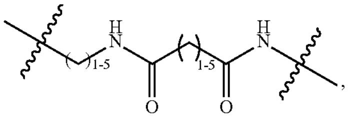

,

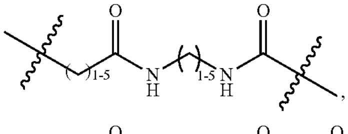

,

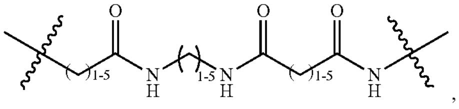

, or

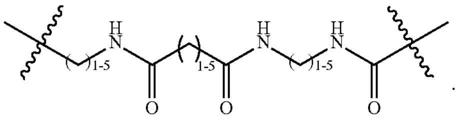

.

The detectable conjugate may have the structure:

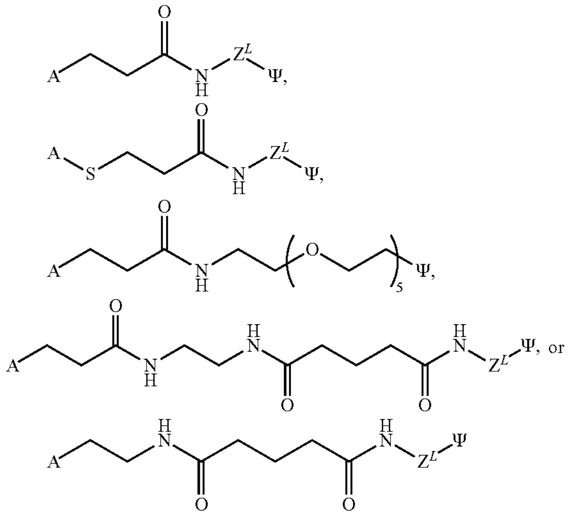

The detectable label may comprise a dimethyl acridinium ester (DMAE) moiety and a zwitterionic linker comprising a zwitterionic linker or a polyethylene glycol derived linker to improve properties of the androstenedione compound (A). Such properties as non-specific binding, hydrophilicity, or compound stability may be improved when ψ comprises a zwitterionic linker or a polyethylene glycol derived linker or a dimethyl phenyl ester. In some embodiments, $Z^L$ has the structure:

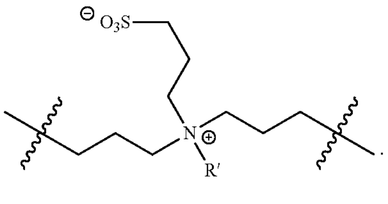

In most embodiment R' is hydrogen or lower alkyl (e.g., methyl, ethyl, propyl, etc.)

In some embodiments, the detectable conjugates may have the structure of formula (III)

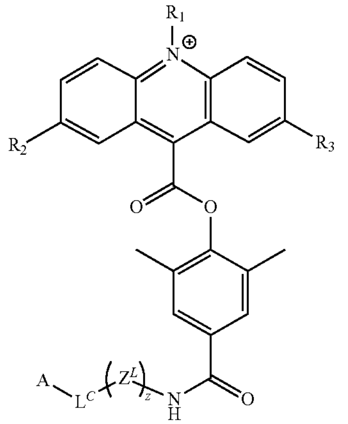

The detectable conjugate may comprise a dimethyl acridinium ester (DMAE) moiety and a zwitterionic linker having the structure of formula (IIIa):

(IIIa)

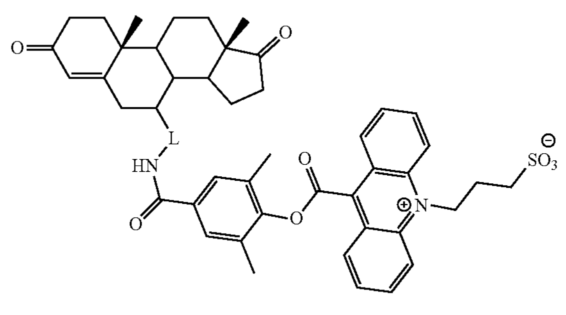

In some embodiments, the structure in formula (IIIa) does not comprise a zwitterionic linker (e.g., L is $L^C$). In some embodiments, L is $L^C$ and $L^C$ comprises $-(CH_2CH_2O)_{1-10}-$ (e.g., $-(CH_2CH_2O)_5-$, etc.), or $-(OCH_2CH_2)_{1-10}-$ (e.g., $-(OCH_2CH_2)_5-$, etc.).

In some embodiments, the compound has the structure of formula (IIIb)

(IIIb)

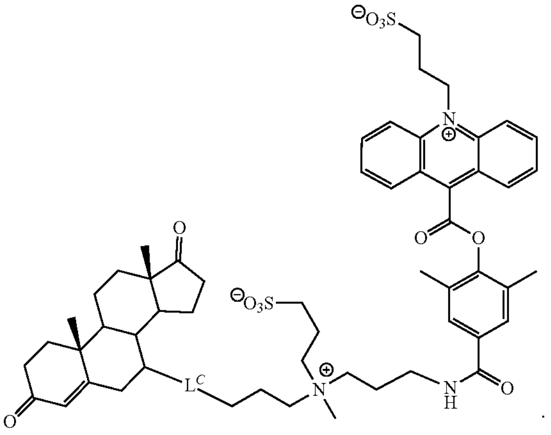

The androstenedione of the detectable label is typically is a monovalent radical of androstenedione (e.g., 4-androstenedionyl). When the point of conjugation is at carbons 3 or 17, the =O attached thereto may be replaced by an =N to form an oxime group. The oxime group may be in either geometrical configuration (i.e., E or Z) or a mixture of the two. In some embodiments, the androstenedione is conjugated to the compound through any one of carbons 3, 6, 7, 19 or 17 of the androstenedione moiety. In some embodiments, the androstenedione is conjugated through any one of carbons 4-16. In preferred embodiments, the androstenedione is conjugated through carbon 6 or 7 the androstenedione. In some embodiments, the A4 is conjugated through the α position of the carbon specified (e.g., 6α, 7α, etc.). In some embodiments, the A4 is conjugated through the β position of the carbon specified (e.g., 6β, 7β, etc.). In some embodiments, the compound is provided as racemic mixture of α and β configurations.

Exemplary compounds are disclosed in Table 1. As used to describe the conjugates, "Z" refers to a zwitterionic linker, "CMO" refers to a carboxy methyl oxime linker, "CME" refers to a carboxy methyl ether linker, "CETE" refers to carboxy ethyl thioether, "ZAE" refers to a zwitterionic acrinidium ester (which is typically an N-sulfopropyl dimethyl acridinium ester in the examples shown ("NSP-DMAE")), "ISODIZAE" refers to an acridinium nucleus with an isopropoxy functional group attached thereto and a full zwitterionic group (comprising both $N^+$ and $X^-$) attached to the positive N of the acridinium nucleus.

TABLE 1

| | |
|---|---|
| 1. A4(3)-CMO-Z-ZAE | 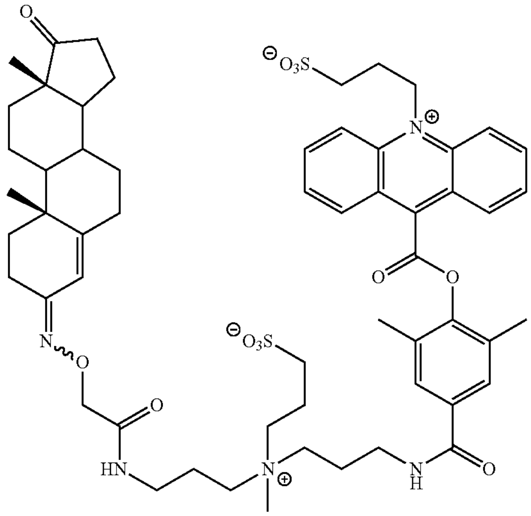 |
| 2. A4(17)-CMO-Z-ZAE | 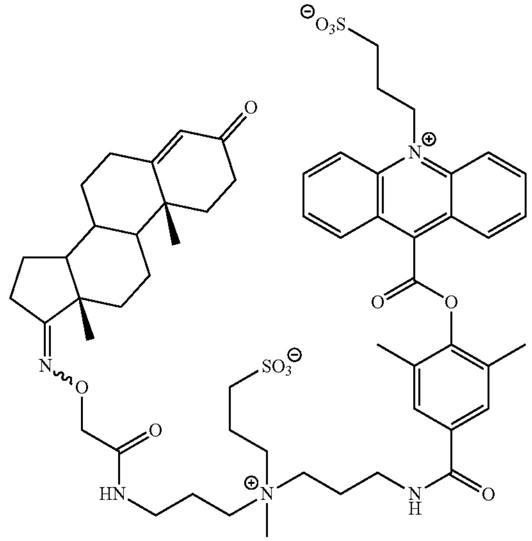 |

TABLE 1-continued
| | |
|---|---|
| 3. A4(19)-CME-NH-Z-ZAE | 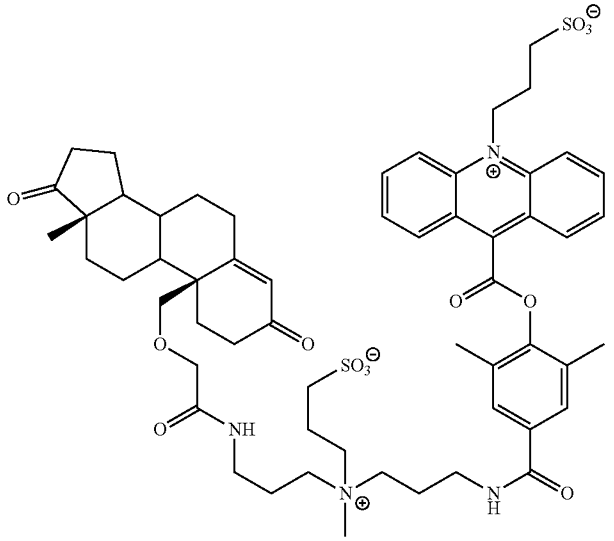 |
| 4. A4(6β)-hemisuccinate-NH-Z-ZAE | 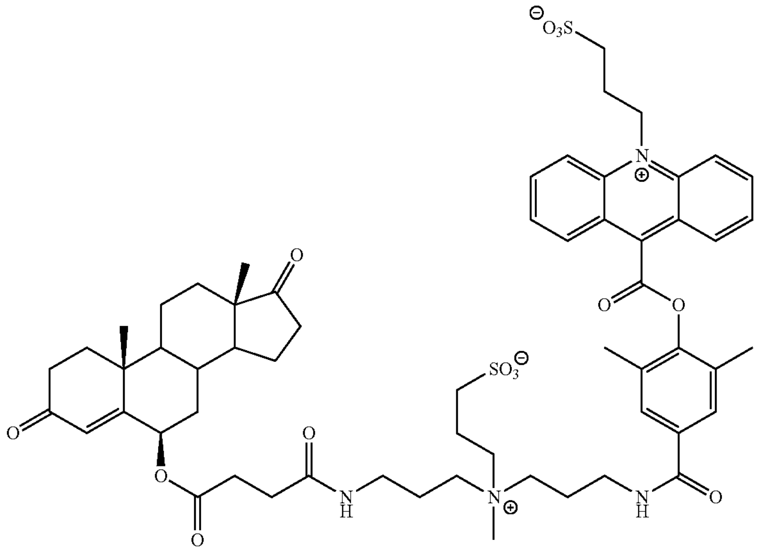 |
| 5. A4(6β)-carbamate-NH-Z-ZAE | 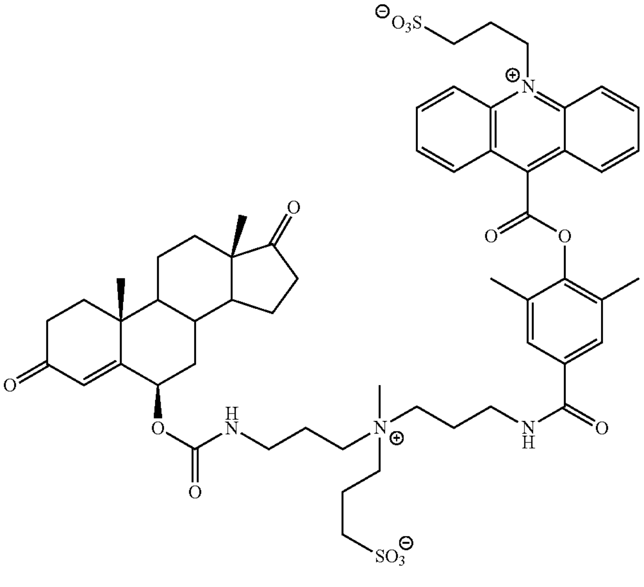 |

TABLE 1-continued
6. A4(6β)-carbamate-Z-ZAE
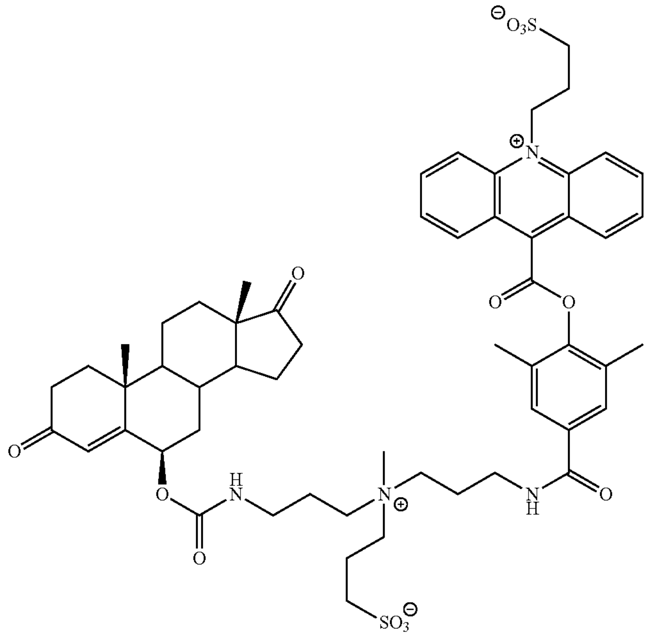
7. A4(7α)-propionamide-Z-ZAE
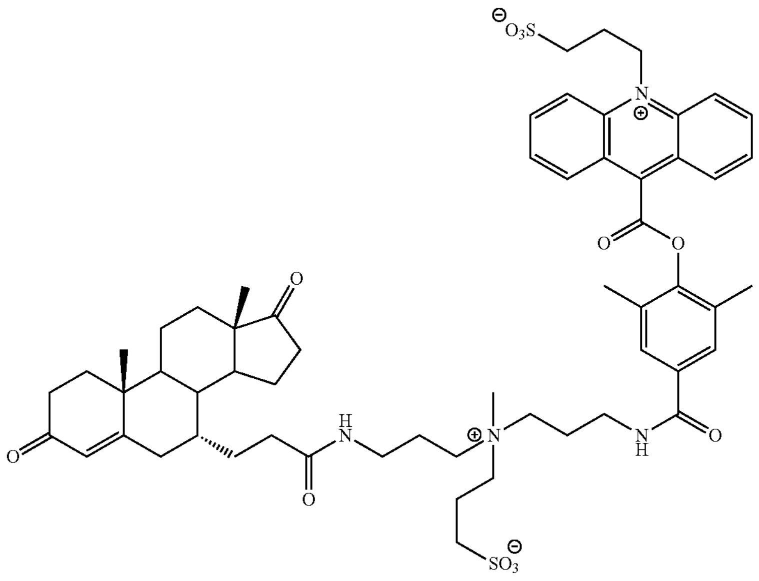

TABLE 1-continued
8. A4(7β)-propionamide-Z-ZAE
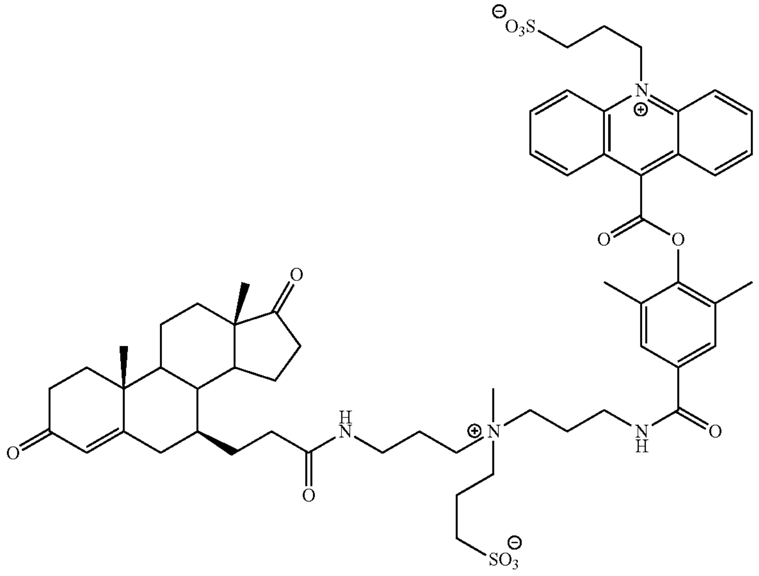
9. A4(7α)-CETE-NH-Z-ZAE
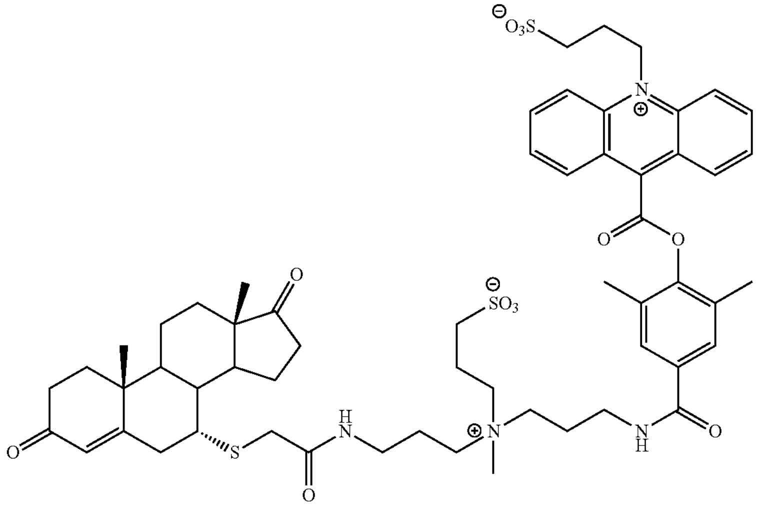
10. A4(7α)-propionamide-HEG-ZAE
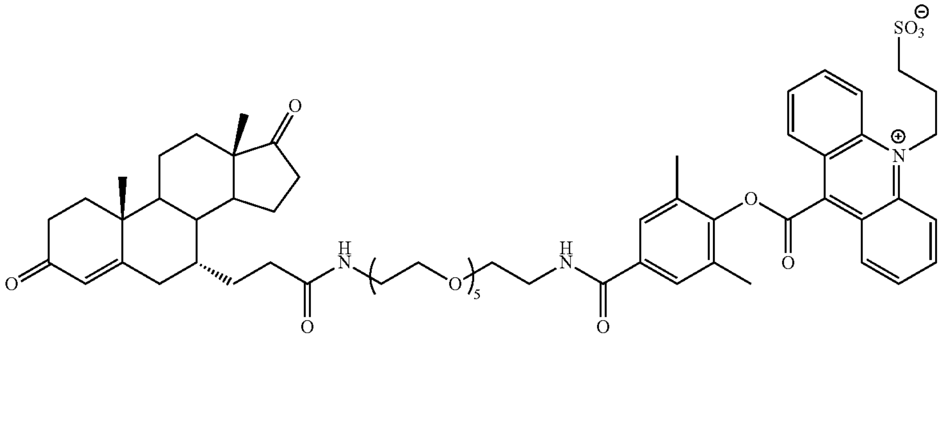

TABLE 1-continued
| | |
|---|---|
| 11. A4(7β)-propionamide-HEG-ZAE | 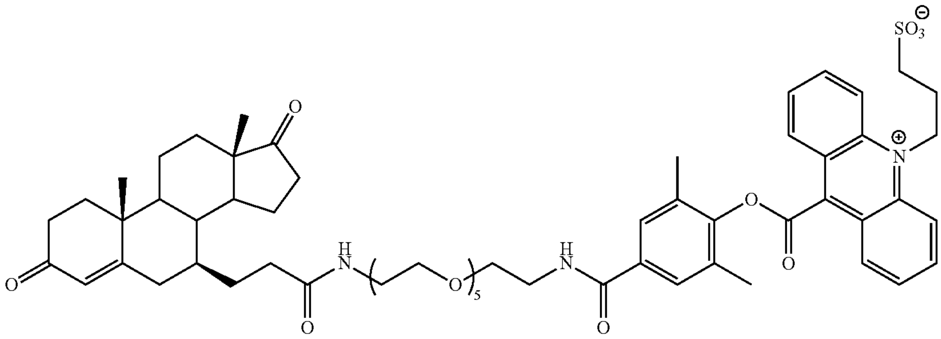 |
| 12. A4(7)-et-NH-glutarate-NH-Z-ISODIZAE | 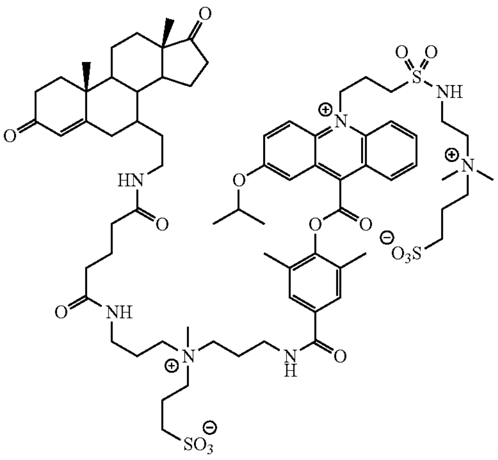 |
| 13. A4(7)-propionamide--et-NH-glutatrate-NH-Z-ISODIZAE | 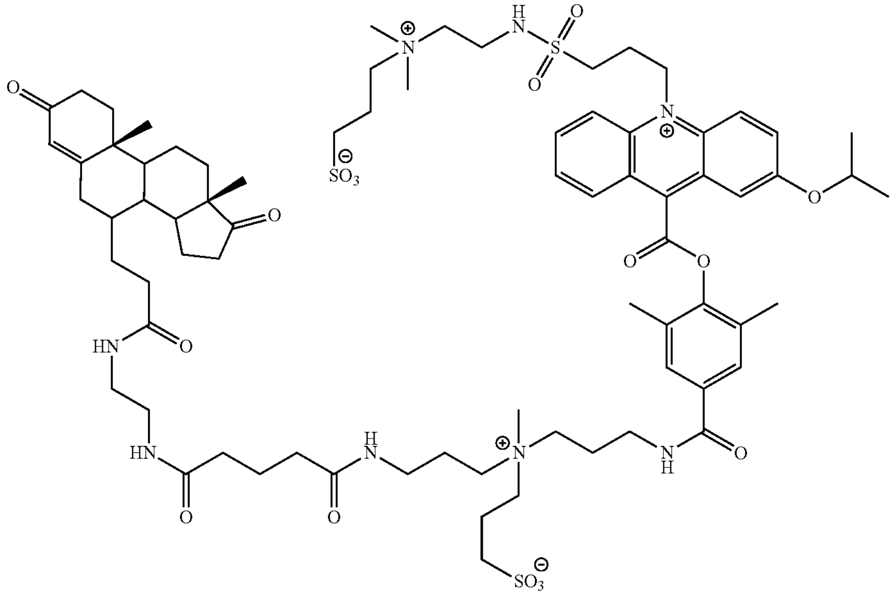 |

The compounds can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations,* 2d. Ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy (FT-IR), spectrophotometry (e.g., UV-visible), or mass spectrometry (MS), or by chromatography such as high pressure liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. For example, the absolute configuration of the stereoisomers may be determined by 1D and 2D NMR techniques such as COSY, NOESY, HMBC and HSQC. Specific implementations of these NMR techniques may be found in Hauptmann, H et al., *Bioconjugate Chem.* 11 (2000): 239-252 or Bowler, J. *Steroids* 54/1 (1989): 71-99, each hereby incorporated by reference in their entirety. Another example method includes preparation of the Mosher's ester or amide derivative of the corresponding alcohol or amine, respectively. The absolute configuration of the ester or amide is then determined by proton and/or $^{19}F$ NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids. Resolution of racemic mixtures can also be carried out by elution on a column packed with an optically active resolving agent (e. g., dinitrobenzoylphenylglycine). Suitable elution solvent compositions can be determined by one skilled in the art.

Exemplary androstenedione derivative starting materials may be obtained from Steraloids, Inc. (Newport, RI). Four androstenedione derivatives used in the synthesis are shown below (the wavy bond designates either configurational isomer or a combination of each isomer):

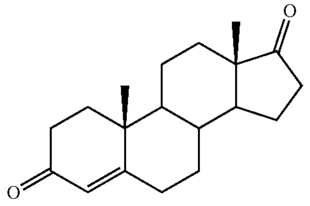

4-androsten-3,17-dione
CAS 63-05-8
Steraloids (A6030-000)

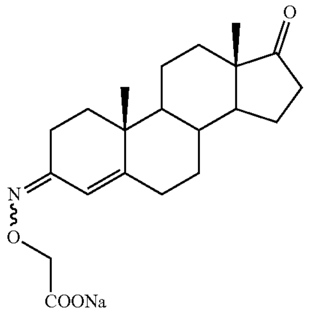

4-androsten-3,17-dione
3-O-carboxymethyloxime, sodium salt
Steraloids (A6035-000)

-continued

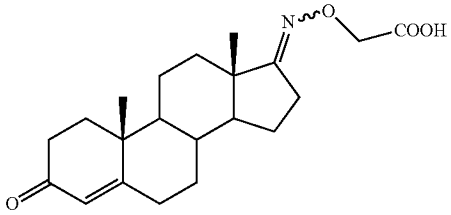

4-androsten-3,17-dione
17-carboxymethyloxime
Steraloids (A6036-400)

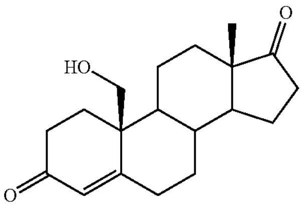

19-hydroxy-4-androsten-3,17-dione
CAS 510-64-5
Steraloids (A6800-000)

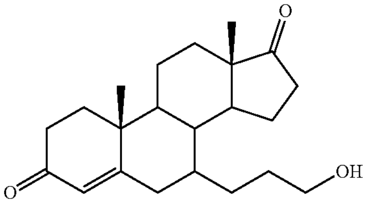

7-hydroxypropyl-4-androsten-3,17-dione

-continued

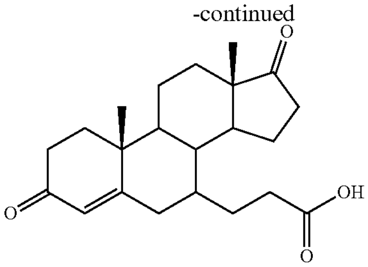

7-carboxyproypl-4-androstene-3,17-dione

Also provided herein are androstenedione conjugates useful for synthesizing the detectable conjugates. These conjugates may have the structure:

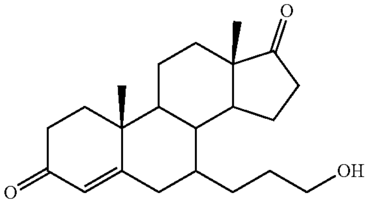

or

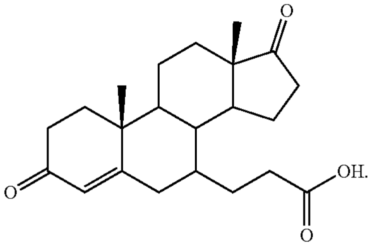

Typically, zwitterionic acridinium esters ("ZAE") comprising a reactive functional group for forming covalent linkages as described in U.S. Pat. No. 6,664,043 to Natrajan et al., U.S. Pat. No. 7,309,615 to Natrajan et al., U.S. Pat. No. 9,575,062 to Natrajan et al., or U.S. Pat. No. 9,487,480 to Natrajan, each hereby incorporated by reference in their entirety and in particular with respect to the zwitterionic acridinium esters described therein and their syntheses, may be used for synthesizing the compounds of the invention. For example, the zwitterionic acridinium ester starting materials may comprise an N-sulfopropyl ("NSP") group in a zwitterionic moiety and/or comprise a charged nitrogen atom connected to the charged acridinium nucleus ("DIZAE") and/or comprise a sterically stabilized dimethyl acridinium ester ("DMAE") and/or comprise an isopropoxy functionalized aciridinium nucleus ("ISO") and/or comprise a zwitterionic ("Z") and/or hexa(ethylene) glycol derived ("HEG") and/or glutarate derived (e.g., $-C(O)-(CH_2)_3-C(O)-$) linking moieties between the acridinium ester and the reactive functional group. The reactive functional group may by $NH_2$ or N-hydroxysuccinimidyl ester ("NHS"). Exemplary acridinium esters which may be used as starting materials are given below in Table 2.

TABLE 2
| Acridinium Esters | Structure |
|---|---|
| NSP-DMAE-Z-$NH_2$ | 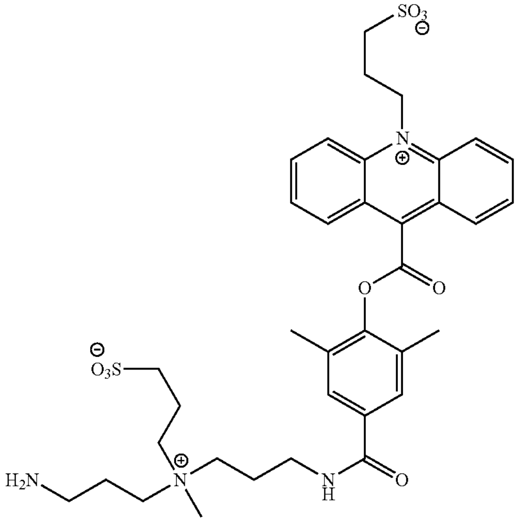 |
| ISODIZAE-Z-NH-glutarate-NHS | 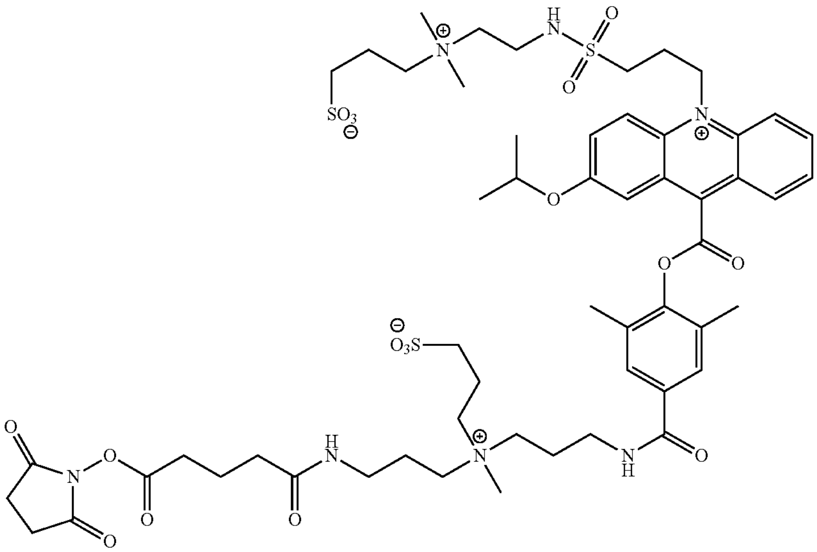 |
| NSP-DMAE-HEG-$NH_2$ | 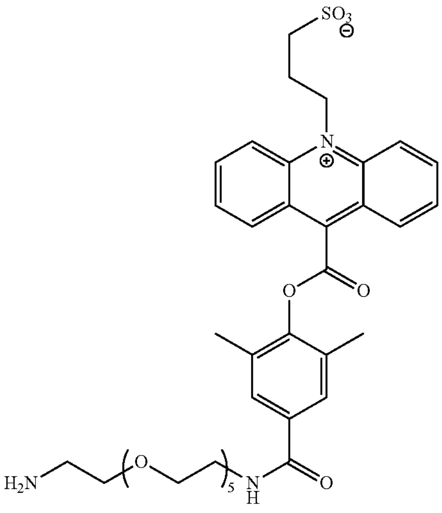 |

The chemiluminescent androstenedione conjugates may also be synthesized through the use of acridinium sulfonamide reactants. For example, the acridinium sulfonamides disclosed in U.S. Pat. No. 5,543,524 to Mattingly et al., hereby incorporated by reference in its entirety, are useful starting materials for the preparation of the chemiluminescent androstenedione conjugates disclosed herein.

The chemiluminescent androstenedione conjugates are useful as labels in assays for the determination or quantitation of certain analytes capable of competing for binding to a binding partner with androstenedione. Most typically, the analyte to be measured is 4-androstenedione.

The assay may be, for example, a 'competitive' immunoassay which typically involves the detection of a large molecule, also referred to as macromolecular analyte, using binding molecules such as antibodies. The antibody is immobilized or attached to a solid phase such as a particle, bead, membrane, microtiter plate, or any other solid surface. A schematic of a competitive assay for androstenedione using the compounds described herein is illustrated in FIG. 1.

In an example of a competitive heterogeneous assay, a support having an antibody for an analyte (e.g., 3C3, 3H10, 4G8 bovine monoclonal antibodies) bound thereto is contacted with a medium containing a sample suspected of containing the analyte and the chemiluminescent androstenedione conjugates (or "labeled analogs") described herein. Analyte from the sample competes for binding to the analyte antibody with the labeled analog. After separating the support and the medium, the label activity of the support or the medium is determined by conventional techniques and is related to the amount of analyte in the sample. In a variation of the above competitive heterogeneous assay, the support comprises the analyte analog, which competes with analyte of the sample for binding to an antibody reagent in accordance with the principles described herein. The labeled analyte analog may be covalently attached with a chemiluminescent or fluorescent molecule often referred to as a label or tracer.

When the solid phase with the immobilized antibody is mixed with a sample containing the analyte and the labeled analyte, a binding complex is formed between the analyte or the labeled analyte. This type of assay is often called a heterogeneous assay because of the involvement of a solid phase. The chemiluminescent signal associated with the binding complex can then be measured and the presence or absence of the analyte in the sample can be inferred. Usually, the binding complex is separated from the rest of the binding reaction components such as excess, labeled analyte, prior to signal generation. For example, if the binding complex is associated with a magnetic bead, a magnet can be used to separate the binding complex associated with the bead from bulk solution.

By using a series of 'standards,' that is, known concentrations of the analyte, a 'dose-response' curve can be generated for the known labeled analyte. Thus, the dose-response curve correlates a certain amount of measured signal with a specific concentration of analyte. In a competitive assay, as the concentration of the analyte increases, the amount of signal decreases if the chemiluminescence from the binding complex is measured. The concentration of the analyte in an unknown sample can then be calculated by comparing the signal generated by an unknown sample containing the macromolecular analyte, with the dose-response curve.

The methodology of the attachment of binding molecules such as antibodies to solid phases is well known in the prior art. For example, an antibody can be covalently attached to a particle containing amines on its surface by using a cross-linking molecule such as glutaraldehyde. The attachment may also be non-covalent and may involve simple adsorption of the binding molecule to the surface of the solid phase, such as polystyrene beads and microtiter plate. Labeling of binding molecules such as antibodies and other binding proteins are also well known in the prior art and are commonly called conjugation reactions and the labeled antibody is often called a conjugate. Typically, an amine-reactive moiety on the label reacts with an amine on the antibody to form an amide linkage. Other linkages, such as thioether, ester, carbamate, and the like between the antibody and the label are also well known in the prior art.

In another aspect of the invention, a reagent is provided for the detection of an analyte comprising a chemiluminescent acridinium compound bound to androstenedione. The reagent may comprise from about 0.1 to about 100 ng/mL of the chemiluminescent acridinium compound or from about 1 to about 50 ng/mL of the chemiluminescent acridinium compound or from about 5 to about 30 ng/mL of the chemiluminescent acridinium compound. In some embodiments, the compound is provided in a reagent which further comprises a buffer.

Typically, the assay for the detection or quantification of an analyte in a sample comprises:

(a) providing a detectable conjugate;
(b) providing a solid support having immobilized thereon an molecule capable of forming a binding complex with said analyte and capable of forming a binding complex with said detectable conjugate;
(c) mixing said compound, said solid support, and said sample;
(d) separating said solid support from said mixture;
(e) triggering chemiluminescence of any acridinium label complexed to said solid phase;
(f) measuring the amount of light emission with a luminometer; and
(g) detecting the presence or calculating the concentration of said analyte by comparing the amount of light emitted with a standard dose response curve which relates the amount of light emitted to a known concentration of the analyte.

Typically, the analyte detected or quantified is androstenedione (e.g., 4-androstenedione, etc.). In some embodiments, the sample derived from a mammal (e.g., human). In some embodiments, the sample comprises saliva and/or blood and/or serum. In some embodiments, the sample is saliva and/or blood and/or serum.

In some assays, the sample to be analyzed is subjected to a pretreatment to release analyte from endogenous binding substances such as, for example, plasma or serum proteins that bind the analyte. The release of the analyte from endogenous binding substances may be carried out, for example, by addition of a digestion agent or a releasing agent or a combination of a digestion agent and a releasing agent used sequentially. The digestion agent is one that breaks down the endogenous binding substances so that they can no longer bind the analyte.

The conditions for conducting an assay on a portion of a sample in accordance with the principles described herein may include carrying out the assay in an aqueous buffered medium at a moderate pH, generally that which provides optimum assay sensitivity. The aqueous medium may be solely water or may include from 0.1 to about 40% by volume of a cosolvent. The pH for the medium may be in the range of about 4 to about 11, or about 5 to about 10, or about 6.5 to about 9.5. Usually, the pH value of the solution will be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include borate, phosphate, carbonate, TRIS, barbital, PIPES, HEPES, MES, ACES, MOPS, and BICINE, for example.

Various ancillary materials may be employed in the assay methods. For example, in addition to buffers, the medium may comprise stabilizers for the medium and for the reagents employed. In some embodiments, the medium may comprise proteins (e.g., albumins), organic solvents (e.g., formamide), quaternary ammonium salts, polyanions (e.g., dextran sulfate), binding enhancers (e.g., polyalkylene glycols), polysaccharides (e.g., dextran, trehalose, etc.), and combinations thereof.

Triggering the chemiluminescence of the analogs may be performed by the addition of a known amount of chemiluminescent triggering reagents. The chemiluminescent triggering reagents may be acidic or basic. Multiple chemiluminescent triggering reagents may be added sequentially. For example, an acidic solution may first be added followed by a basic solution. In some embodiments, the chemiluminescent triggering reagents comprise hydrogen peroxide, hydrogen peroxide salts, nitric acid, nitric acid salts, sodium hydroxide, ammonium salts, or combinations thereof.

EXAMPLES

The following Examples illustrate the synthesis of a representative number of compounds and the use of these compounds in the measurement of androstenedione samples in heterogeneous competitive assay. Accordingly, the Examples are intended to illustrate but not to limit the disclosure. Additional compounds not specifically exemplified may be synthesized using conventional methods in combination with the methods described herein.

Example 1: Synthesis of A4(7)-propionic Acid Intermediate

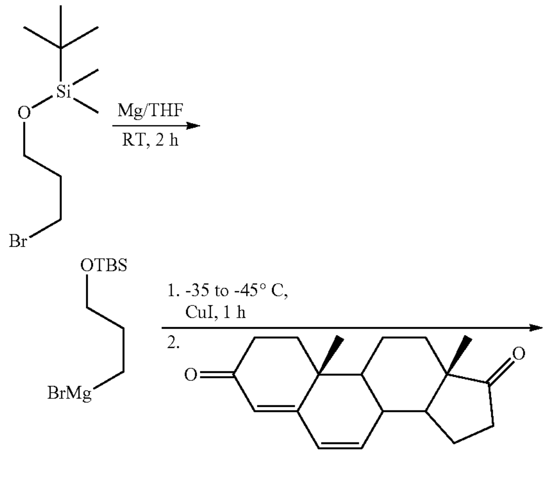

-continued

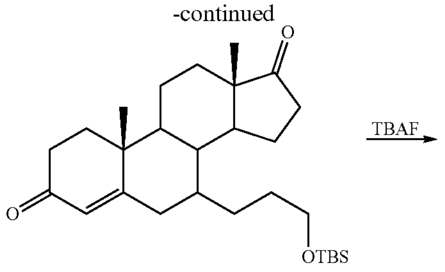

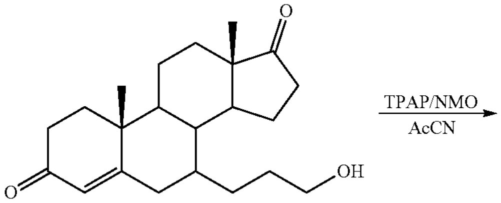

7-hydroxypropyl-4-androstene-3,17-dione

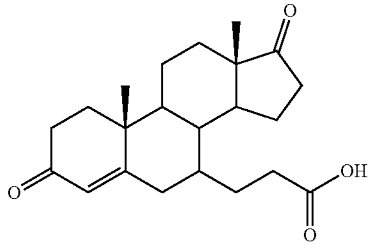

7-carboxypropyl-4-androstene-3,17-dione (3-Bromopropoxy)-tert-butyldimethylsilane (1654 mg, 6.53 mmol) was added to a round bottom flask (RBF) charged with a stir bar, magnesium, turnings (164 mg, 6.82 mmol), and anhydrous THF (6 mL) with stirring at 40° C. The resulting mixture was stirred at 40° C. until most of the magnesium turnings disappeared. The reaction mixture was cooled down to room temperature (RT). More THF (10 mL) was added to dissolve any precipitate to form a homogeneous Grignard regent solution. This Grignard regent solution (16 mL) was added to a suspension of CuI (597 mg, 3.14 mmol) in THF (10 mL) at −40° C. to −30° C. over 15 min. The resulting mixture was stirred for 10 min at −40° C. to −30° C. to form an organocuprate solution. 4, 6-androstadien-3,17-dione (150 mg in 1 mL THF solution, 0.53 mmol) was then added to the organocuprate solution. The resulting mixture was stirred for 1 h at −40° C. to −30° C. Glacial acetic acid (AcOH, 2 mL) was added to the reaction at −40° C. to −30° C. with stirring. The resulting mixture was stirred for 30 min. Saturated aq. $NH_4Cl$ solution (30 mL) was added and stirred 20 more min at RT. The resulting mixture was extracted three times with methyl t-butyl ether (MTBE). The combined MTBE extracts solution was washed with saturated brine (2×), dried over $Na_2SO_4$, filtered, and concentrated to give the crude product. This crude was purified by Silica Gel flash chromatography (Hexanes/Ethyl acetate) to give the pure desired product A4-7-PrOTBS as a mixture of a and 13 (181 mg, 74%). MS (M+H, 459.3).

THF solution of 1.0 M (1.5 mL, 1.5 mmol) was added to a solution of A4-7-PrOTBS (176 mg, 0.384 mmol) in THF (2 mL) with stirring at 0° C. (ice-bath). The resulting mixture was removed from the ice-bath and stirred at RT for 1 h. Saturated brine (8 mL) was added to the reaction. The resulting mixture was stirred for 30 min and then extracted with EtOAc three times. The combined EtOAc extracts solution was washed saturated brine (2×), dried over $Na_2SO_4$, filtered, and concentrated to give the crude product. This crude was purified by Silica Gel flash chromatography (Hexanes/EtOAc) to give the pure desired product A4-7-PrOH as a mixture of α and β (92.9 mg, 70%). MS (M+Na, 367.2).

A4-7-PrOH (87.5 mg, 0.255 mmol) was dissolved in MeCN (3 mL). Tetrapropylammonium perruthenate ("TPAP," 18.9 mg, 0.0538) was dissolved in MeCN (2 mL). The TPAP MeCN solution was added to N-methylmorpholine N-oxide ("NMO") mono hydrate (366 mg, 2.71) with stirring to dissolve all solids. The NMO-TPAP solution was then added to A4-7-PrOH solution with stirring. The resulting mixture was stirred for That RT. After 1 h, 2-PrOH (1 mL) was added to the mixture solution and stirred for 1 h to quench the excess NMO. The reaction mixture solution was directly loaded into a dry silica gel cartridge. Washed the silica gel cartridge with 5% HOAc in EtOAc. The collected 5% HOAc in EtOAc solution was concentrated to give the crude product This crude was purified by HPLC (00.05% TFA in water/0.05% TFA in MeCN) to give the pure desired product A4-7-propionic acid as a mixture of α and β (51.6 mg, 57%). MS (M+Na, 367.2).

Example 2: Synthesis of A4(3)-CMO-Z1-ZAE Conjugate

Synthesis of A4(3)-carboxy methyl oxime ("CMO")-Z-ZAE conjugate was performed using the synthetic schema described below.

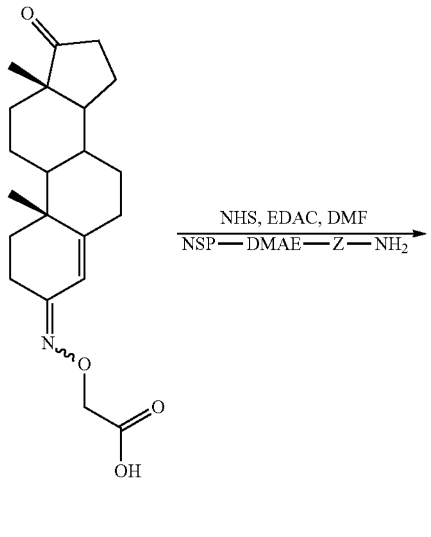

-continued

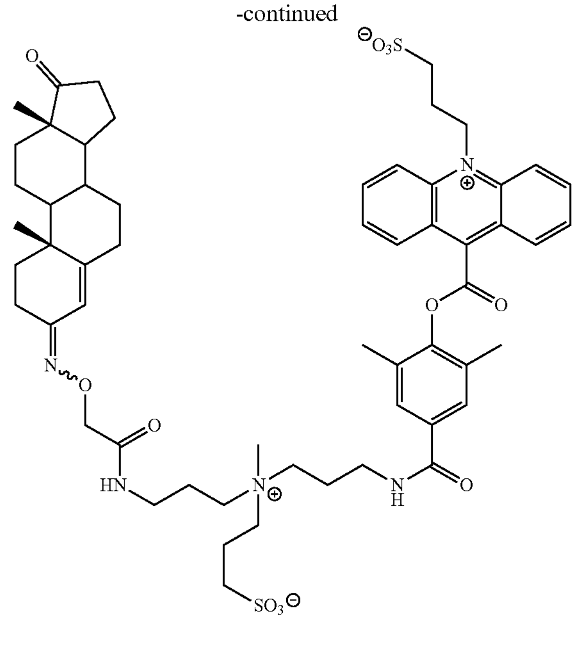

The A4(3)-CMO-Z-ZAE conjugate was also synthesized by reacting 4-androsten-3,17-dione 3-O-carboxymethyloxime, sodium salt with NSP-DMAE-Z-$NH_2$ in the presence of (benzotriazol-1-yloxy)tris(dimethylamino)phosphonium hexafluorophosphate ("BOP"), N,N-diisopropylethylamine ("$(iPR)_2NEt$"), and N,N-dimethylformamide ("DMF"). A 10% $H_2O$:90% DMF solution (vol:vol) was prepared by mixing 100 μL of $H_2O$ with 900 μL of DMF. A mixture of 4-androsten-3,17-dione 3-O-carboxymethyloxime, sodium salt (1.1 mg, 2.9 μmol), NSP-DMAE-Z-$NH_2$ (1.3 mg, 1.7 μmol), and BOP (1.7 mg, 3.8 μmol) was added to 333 μL of the $H_2O$:DMF solution. The solution was mixed thoroughly and the $(iPr)_2NEt$ (0.9 μL, 0.7 mg, 5.4 μmol) was added. Upon addition of the $(iPr)_2NEt$ base, the solution turned from yellow to colorless. The reaction mixture was stirred at room temperature overnight for 19.1 hours.

After overnight stirring, analytical high pressure liquid chromatography ("HPLC") was performed on the reaction mixture using a Phenomenex Bondclone $C_{18}$, 10 μm, 300× 3.9 mm column and a multistep gradient (0%→39% B in 39 minutes; 39%→100% B in 1 minute; hold at 100% B for 6 minutes) of eluents (A=water with 0.05% trifluoracetic TFA; B=acetonitrile with 0.05% TFA) at a flow rate of 1.0 mL/minute, an injection loop size of 250 μL, and a detection wavelength of 260 nm. Analytical HPLC showed 90% conversion to product. The mixture was stored at −70° C. for 72 hours. Purification with semi preparative HPLC was performed on the reaction mixture. Preparative HPLC was performed on the reaction mixture using a YMC-Pack ODS-A, No. 3025000136 (W), $C_{18}$ 10 μm 250×30 mm column and a 10% B→70% B over 50 minutes gradient of eluents (A=water with 0.05% trifluoracetic TFA; B=acetonitrile with 0.05% TFA) at a flow rate of 20.0 mL/minute, an injection loop size of 5 mL, and a detection wavelength of 262 nm. The product eluted as two isomeric peaks at retention times of 34.1-34.9 min. Peak fractions were collected, frozen at −70° C. and lyophilized to produce two separate yellow powders (65% total yield). HPLC and matrix-assisted laser desorption/ionization TOF-MS ("MALDI TOF-MS") were used to characterize each fraction. For MALDI TOF-MS analysis, each sample was dissolved in 1:1 acetonitrile+0.05% trifluoroacetic acid: water+

0.05% trifluoroacetic acid at concentration of 0.05-2.00 mg/mL. This mixture was mixed in approximately 1:1 ratio with an α-cyano-4-hydroxycinnamic acid ("HCCA") matrix solution and spot on target plate. The concentrations were adjusted as needed to generate good signal to noise. The MALDI TOF-MS was run at positive ion linear or reflective modes. The fraction with a retention time of 34.15 minutes (93.54% pure) had a MALDI TOF-MS peak of 1085.426 (linear positive mode) and 1084.990 (reflector positive mode). The fraction with a retention time of 34.05 minutes (89.63% pure) had a MALDI TOF-MS peak of 1084.782 (linear positive mode) and 1084.704 (reflector positive mode).

Example 3: Synthesis of A4(17)-CMO-Z-ZAE Conjugate

Synthesis of A4(17)-CMO-Z-ZAE conjugate was performed using the synthetic schema described below.

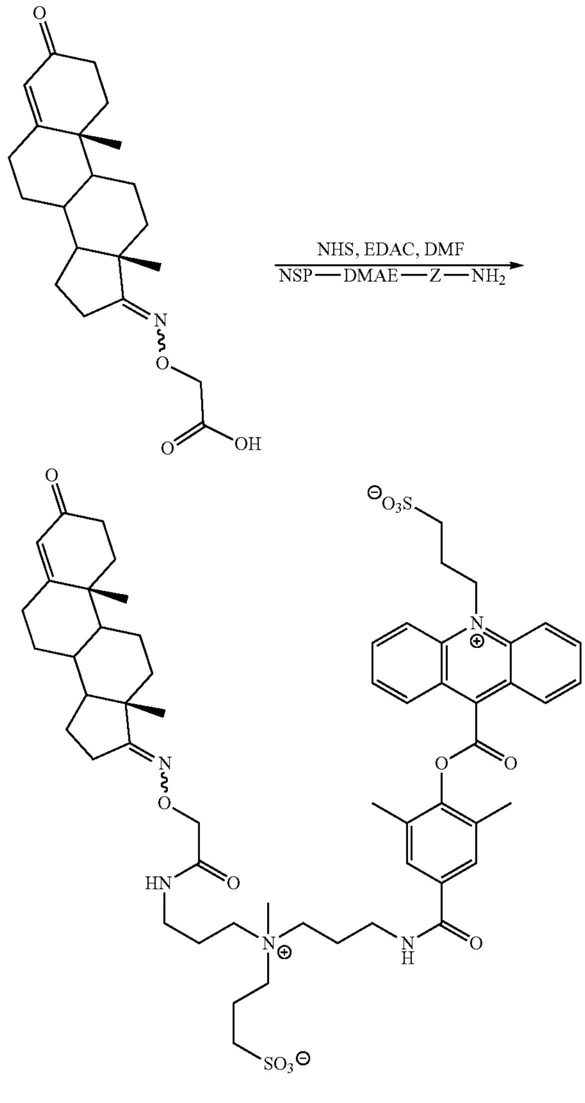

The A4(17)-CMO-Z-ZAE conjugate was also synthesized by reacting 4-androsten-3,17-dione 17-carboxymethoxyloxime with NSP-DMAE-Z-$NH_2$ in the presence of (benzotriazol-1-yloxy)tris(dimethylamino)phosphonium hexafluorophosphate ("BOP"), N,N-diisopropylethylamine ("$(iPR)_2$ NEt"), and N,N-dimethylformamide ("DMF"). A 10% $H_2O$: 90% DMF solution (vol:vol) was prepared by mixing 100 μL of $H_2O$ with 900 μL of DMF. A mixture of 4-androsten-3,17-dione 17-carboxymethoxyloxime (1.1 mg, 3.1 μmol), NSP-DMAE-Z-$NH_2$ (1.3 mg, 1.7 μmol), and BOP (1.9 mg, 4.3 μmol) was added to 333 μL of the $H_2O$:DMF solution. The solution was mixed thoroughly and the $(iPr)_2NEt$ (0.9 μL, 0.7 mg, 5.4 μmol) was added. Upon addition of the $(iPr)_2NEt$ base, the solution turned from yellow to colorless. The reaction mixture was stirred at room temperature overnight for 20.2 hours.

After overnight stirring, analytical high pressure liquid chromatography ("HPLC") was performed on the reaction mixture using a Phenomenex Bondclone $C_{18}$, 10 μm, 300×3.9 mm column and a multistep gradient (0% B for 1 minute; 0%→60% B in 60 minutes; 60%→100% B in 3 minutes; hold at 100% B for 6 minutes) of eluents (A=water with 0.05% trifluoracetic TFA; B=acetonitrile with 0.05% TFA) at a flow rate of 1.0 mL/minute, an injection loop size of 250 μL, and a detection wavelength of 260 nm. Analytical HPLC showed 65% conversion to product. The mixture was stored at −70° C. for 72 hours. Purification with semi preparative HPLC was performed on the reaction mixture. Preparative HPLC was performed on the reaction mixture using a YMC-Pack ODS-A, No. 3025000136 (W), $C_{18}$ 10 μm 250×30 mm column and a 10% B→70% B over 50 minutes gradient of eluents (A=water with 0.05% trifluoracetic TFA; B=acetonitrile with 0.05% TFA) at a flow rate of 20.0 mL/minute, an injection loop size of 5 mL, and a detection wavelength of 262 nm. The product eluted a peak at retention times of 32.7-34.0 min. The peak fraction was collected, frozen at −70° C. and lyophilized to produce a yellow powder (1.2 mg, 65% total yield). HPLC and MALDI TOF-MS were used to characterize the fraction. The fraction had a MALDI TOF-MS peak of 1084.718 (linear positive mode) and 1084.722 (reflector positive mode).

Example 4: Synthesis of A4(19)-CME-Z-ZAE Conjugate

Synthesis of A4(19)-carboxy methyl ether ("CME")-Z-ZAE conjugate was performed using the synthetic schema described below.

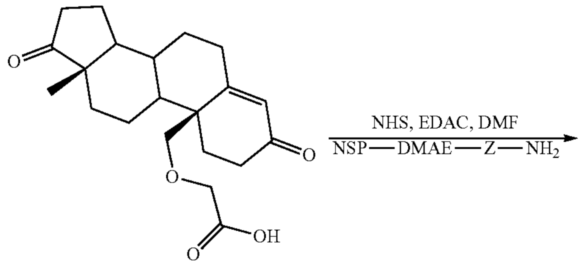

-continued

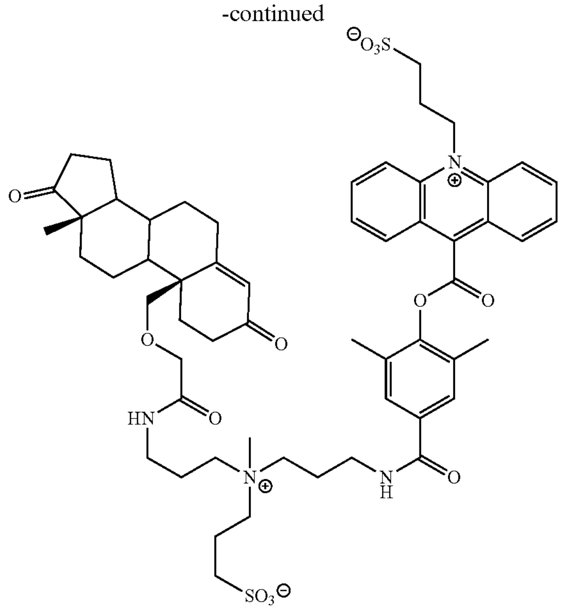

The A4(17)-CMO-Z-ZAE conjugate was also synthesized by reacting 3,17-dioxo-4-androsten-19-yl carboxymethyl ether with NSP-DMAE-Z-$NH_2$ in the presence of (benzotriazol-1-yloxy)tris(dimethylamino)phosphonium hexafluorophosphate ("BOP"), N,N-diisopropylethylamine ("OPR)$_2$ NEt"), and N,N-dimethylformamide ("DMF"). 3,17-dioxo-4-androsten-19-yl carboxymethyl ether was synthesized as disclosed in RA4, Pemmaraju Narasimha, et al. *Journal of Steroid Biochemistry* 17(5), 523-527 (1982), hereby incorporated by reference in its entirety and in respect to androstenedione conjugate synthesis. A 10% $H_2O$:90% DMF solution (vol:vol) was prepared by mixing 100 μL of $H_2O$ with 900 μL of DMF. A mixture of 3,17-dioxo-4-androsten-19-yl carboxymethyl ether (6.8 mg, 1.9 μmol), NSP-DMAE-Z-$NH_2$ (13.8 mg, 18.6 μmol), and BOP (13.3 mg, 30.1 μmol) was added to 952 μL of the $H_2O$:DMF solution. The solution was mixed thoroughly and the (iPr)$_2$NEt (9.6 μL, 7.1 mg, 5.5 μmol) was added. Upon addition of the (iPr)$_2$NEt base, the solution turned from yellow to colorless.

After 1.5 hours, Analytical HPLC showed 94% conversion to product. Analytical HPLC was performed on the reaction mixture using a Phenomenex Bondclone $C_{18}$, 10 μm, 300×3.9 mm column and a multistep gradient (0% B for 1 minute; 0%→100% B in 30 minutes; hold at 100% B for 6 minutes) of eluents (A=water with 0.05% trifluoracetic TFA; B=acetonitrile with 0.05% TFA) at a flow rate of 1.0 mL/minute, an injection loop size of 250 μL, and a detection wavelength of 260 nm. Analytical HPLC showed 94% conversion to product. The mixture was stored at −70° C. for 24 hours. Purification with semi preparative HPLC was performed on the reaction mixture. Preparative HPLC was performed on the reaction mixture in two injections using a YMC-Pack ODS-A, No. 3025000136 (W), $C_{18}$ 10 μm 250×30 mm column and a 10% B→70% B over 50 minutes gradient of eluents (A=water with 0.05% trifluoracetic TFA; B=acetonitrile with 0.05% TFA) at a flow rate of 20.0 mL/minute, an injection loop size of 5 mL, and a detection wavelength of 261 nm. The product eluted a peak at retention times of 21.9-23.8 min. The peak fraction was collected, frozen at −70° C. and lyophilized to produce a yellow powder (7.0 mg, 35% total yield). HPLC and MALDI TOF-MS were used to characterize the fraction. The fraction had a MALDI TOF-MS peak of 1085.400 (linear positive mode) and 1085.382 (reflector positive mode).

Example 5: Synthesis of A4(6β)-hemisuccinate-Z-ZAE Conjugate

Synthesis of A4(6β)-hemisuccinate-Z-ZAE conjugate was performed using the synthetic schema described below.

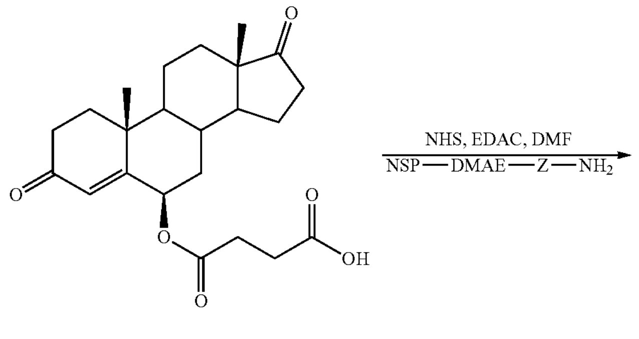

-continued
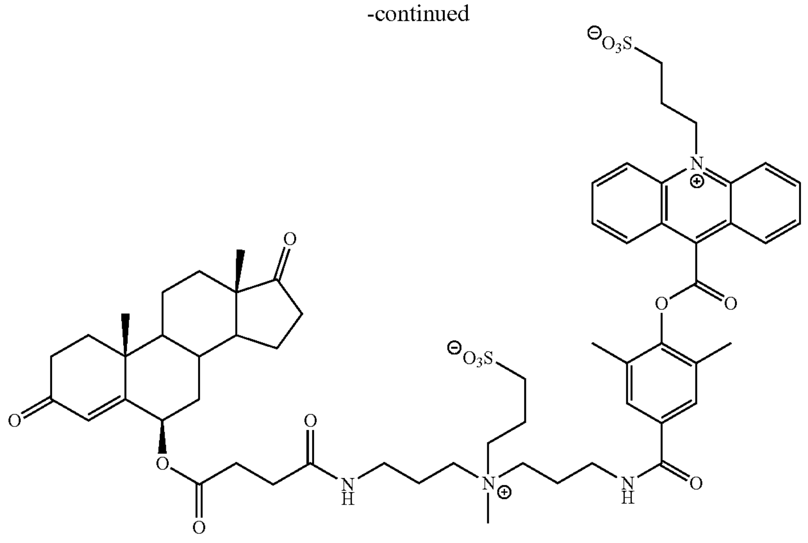
Example 6: Synthesis of A4(6β)-carbamate-Z1-ZAE Conjugate
Synthesis of A4(6β)-carbamate-Z-ZAE conjugate was performed using the synthetic schema described below.
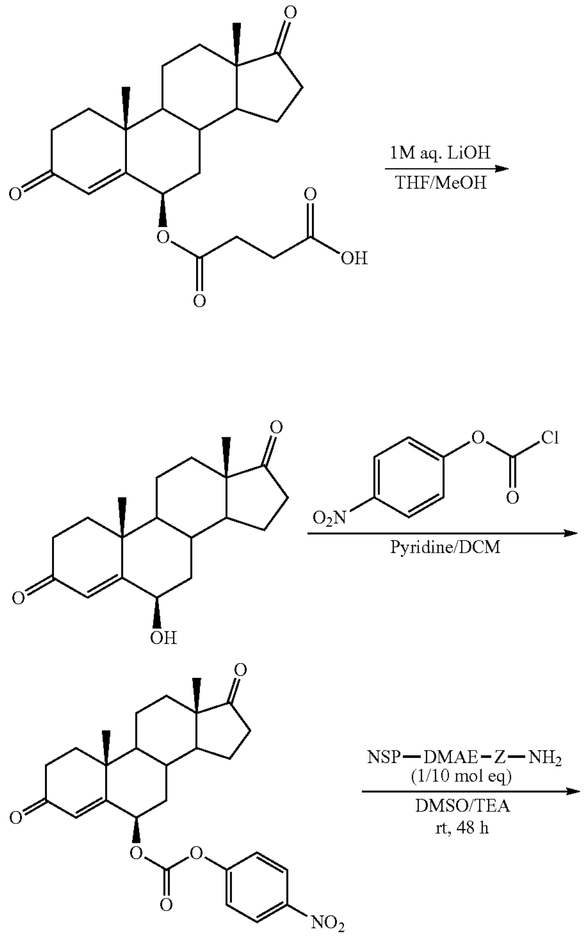
-continued
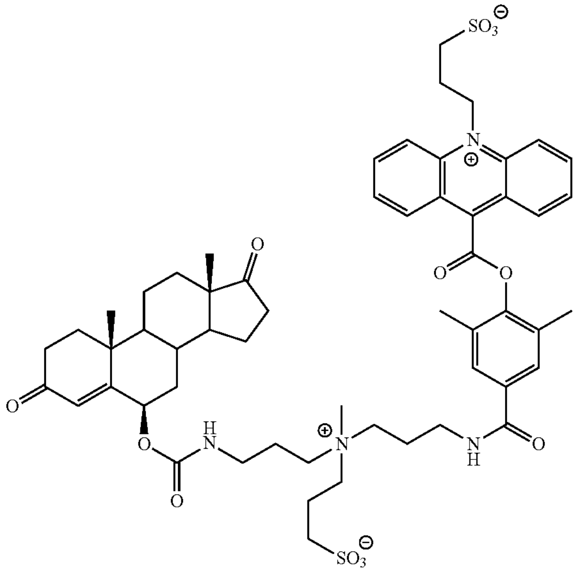
Example 7: Synthesis of A4(7α)-CETE-ZAE Conjugate
Synthesis of A4(7α)-carboxy ethyl thio ether ("CETE")-NH-Z-ZAE conjugate was performed using the synthetic schema described below.
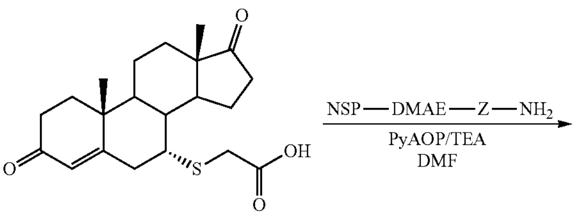

-continued

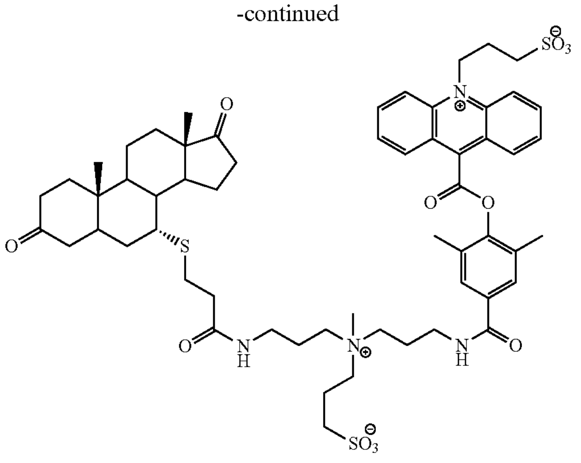

Example 8: Synthesis of A4(7)-propionamide-Z-ZAE Conjugate

Synthesis of A4(7)-propionamide-Z-ZAE conjugate was performed using the synthetic schema described below.

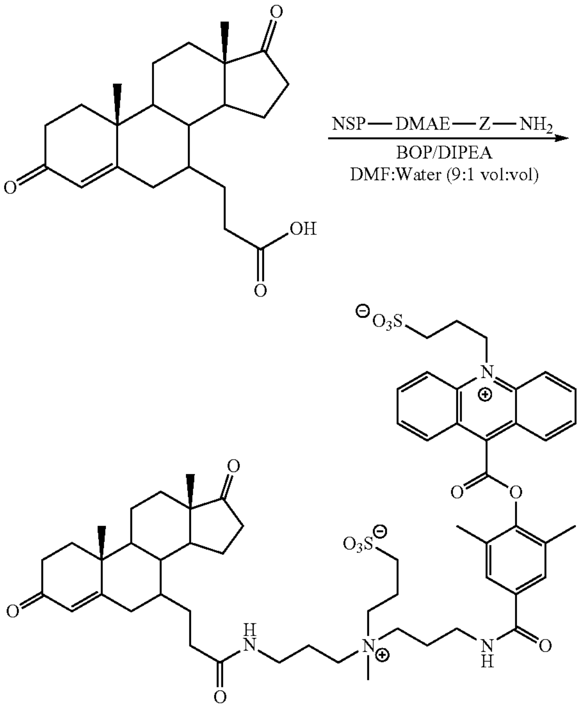

DMF-water mix solvent (9/1, 0.6 mL) and N,N-diisopropylethylamine ("DIPEA," 4.7 μL, 26.9 μmole) were added to a vial charged with NSP-DMAE-Z-$NH_2$ (5.0 mg, 6.73 μmole), A4 7-propionic acid (2.51 mg, 7.01 μmole), and (Benzotriazol-1-yloxy)tris(dimethylamino)phosphonium hexafluorophosphate ("BOP," 5.97 mg, 13.5 μmole) with stirring. The resulting mixture was stirred for 4 hours at RT. This reaction mixture was directly purified by HPLC (00.05% TFA in water/0.05% TFA in MeCN) to give the pure desired product A4-7-propionic acid as a mixture of α and β (4.36 mg, 60%). MS (M+Na, 1105.5).

Example 9: Synthesis of A4(7)-propionamide-HEG-ZAE Conjugates

Synthesis of A4(7)-propionamide-HEG-Z-ZAE conjugate was performed using the synthetic schema described below.

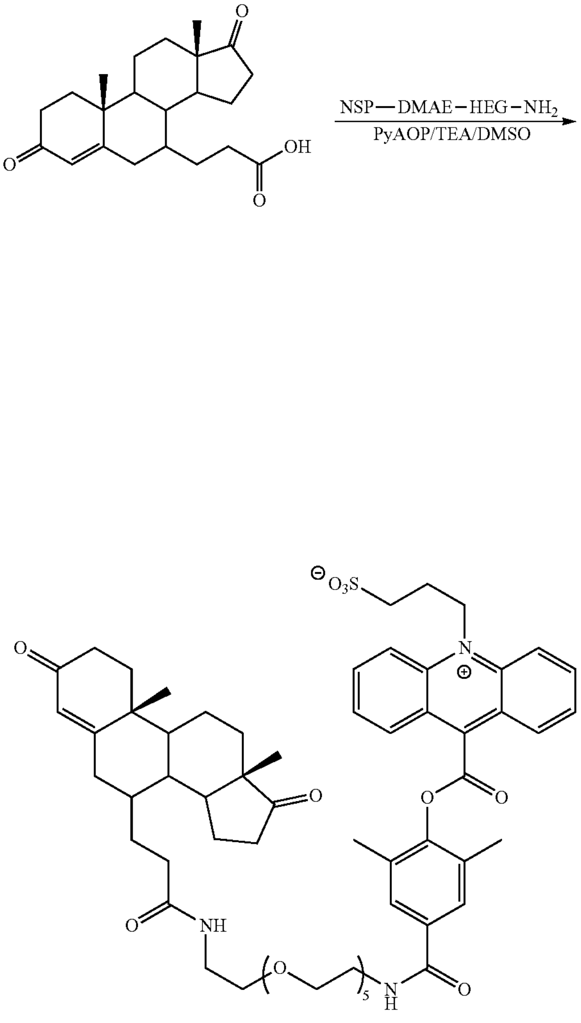

Example 10: Synthesis of A4(7)-propionamide-et-NH-glutarate-NH-Z-ISODIZAE Conjugate DMSO (1.0 mL) and TEA (30 μL) were added to a vial charged with NSP-DMAE-HEG-$NH_2$ (1.5 mg, 1.98 μmole), A4 7-propionic acid (5.4 mg, 14 μmole), and (7-azabenzotriazol-1-yloxy)tripyrrolidino-phosphonium hexafluorophosphate ("PyA4P," 23.1 mg, 44.3 μmole) with stirring. The resulting mixture was stirred for 4 hours at RT. This reaction mixture was directly purified by HPLC (00.05% TFA in water/0.05% TFA in MeCN) to give the pure desired product A4-7-propionic acid as a mixture of α and β (1.55 mg, 40%). MS (M+Na, 1118.6).

Synthesis of A4(7)-propionamide-et-NH-glutarate-NH-Z-ISODIZAE conjugate was performed using the synthetic schema described below.

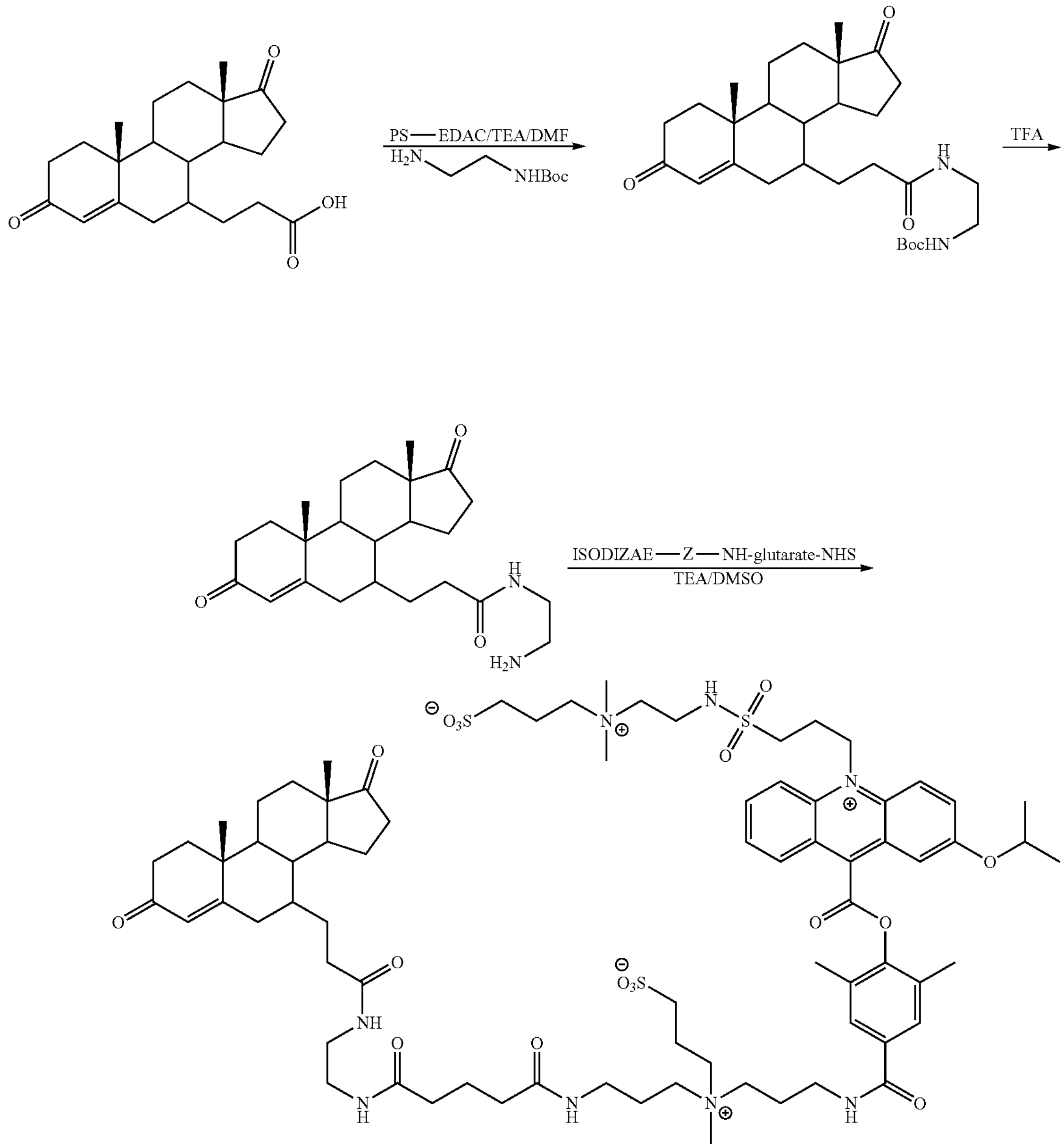
Example 11: Synthesis of A4(7)-et-NH-glutarate-NH-Z-ISODIZAE Conjugate
Synthesis of A4(7)-et-NH-glutarate-NH-Z-ISODIZAE conjugate was performed using the synthetic schema described below.
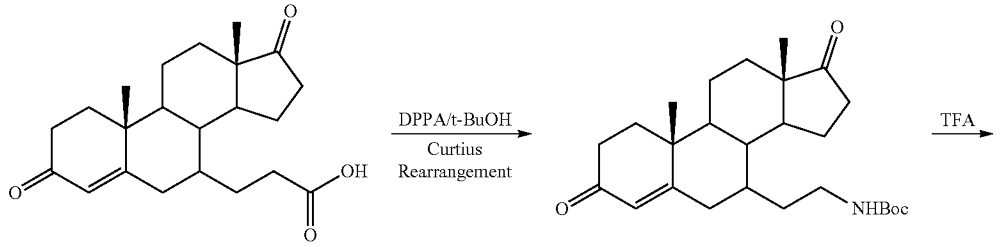

-continued

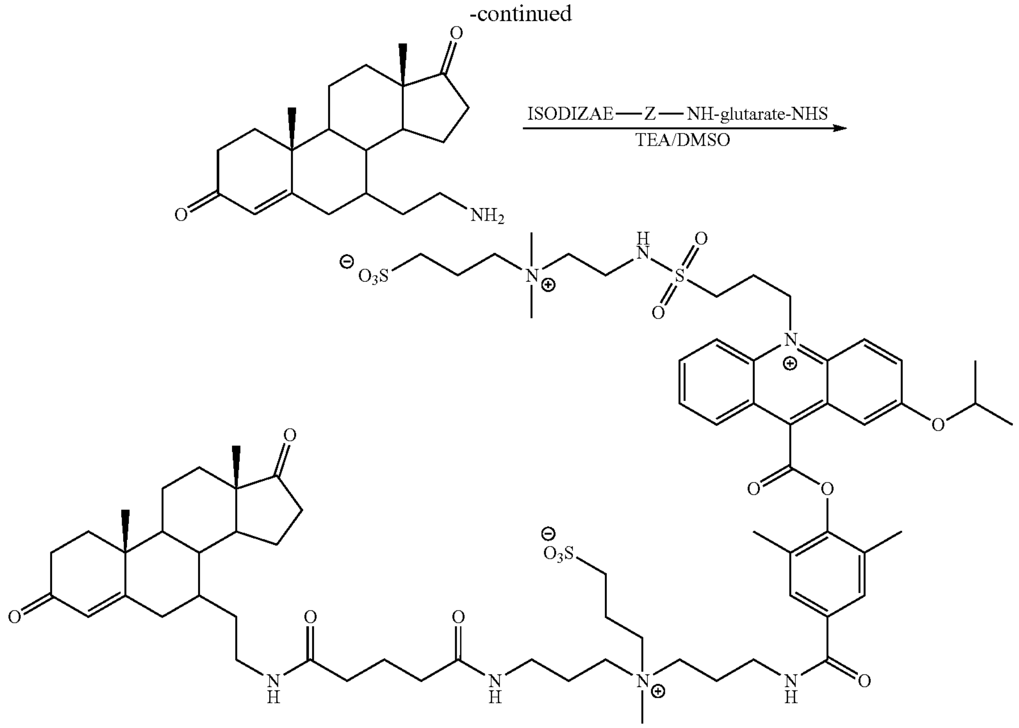

Example 12: Evaluation of A4-AE Conjugates

Evaluation of A4-AE conjugates was performed using the ADVIA Centaur family of immunoassay analyzers (available from Siemens Healthcare Diagnostics Inc., Tarrytown, NY) using a competitive assay format which utilizes a solid phase reagent and a lite reagent. The lite reagent comprises 20 ng/mL of an A4-AE tracer compound. The solid reagent comprises superparamagnetic beads (Dynabeads® M-270 Streptavidin available from ThermoFisher Scientific) labeled with biotinylated monoclonal anti-A4 antibody. Biotinylated sheep monoclonal androstenedione antibodies 3C3, 3H10, or 4G8 (available from Bioventix, UK) are introduced to the streptavidin coated superparamagnetic beads in order to produce solid phase particles attached to the antibody. Solid phase particles mixed with A4-AE in the absence of A4, results in solid phase binding complexes with the A4-AE compounds. When the lite reagent comprises androstenedione, competition for formation of a binding complex at each antibody occurs between A4 and A4-AE conjugates. As can be seen in FIG. 1, a solid phase particle ("SP") with more androstenedione binding complexes will comprise less chemiluminescent acridinium moieties (circled in FIG. 1). Therefore, an increase in androstenedione concentration in measured samples correlates with a decrease in chemiluminescence of separated and washed solid phase particles binding complexes. Chemiluminescence of the separated solid phase particle binding complexes is induced by addition of an acidic solution (0.5% Peroxide/0.45% Nitric Acid (vol/vol)) followed by a basic solution (0.25N NA4H/0.45% ARQUAD® 16-50 (w/v)) and measured. Reagent volumes, concentrations, and assay parameters were otherwise identical in each experiment other than variation of the A4-AE tracer conjugate measured. Samples of androstenedione used in the lite reagent were prepared using a human serum albumin-based matrix (available from Bioresource Technology, Inc.) with the androstenedione sample concentrations shown in FIGS. 2A-2D (ng/mL).

Chemiluminescence was monitored for a variety of A4-AE conjugates. Table 2 below and the corresponding FIGS. 2A-2D summarize the results of chemiluminescent experiments on several A4-AE conjugates which may be synthesized as described in the indicated Example number. In Table 3 a "+" indicates appreciable binding of the specified A4-AE conjugate to the specified antibody and a "–" indicates no appreciable binding was observed.

TABLE 3

| Ex. No. | A4 Conjugate Position | Linker Moiety | 3C3 | 3H10 | 4G8 | FIG. |
|---|---|---|---|---|---|---|
| 5 | 6 | —OC(O)NH— | – | – | – | |
| 2 | 17 | =NO(C(O)NH— | – | – | – | |
| 1 | 3 | =NOCH$_2$C(O)NH— | + | + | – | 2A |
| 3 | 19 | —OCH$_2$C(O)NH— | – | + | + | 2B |
| 4 | 6β | —OC(O)CH$_2$CH$_2$C(O)NH— | + | + | + | 2C |
| 6 | 7α | —SCH$_2$CH$_2$C(O)NH— | + | + | + | 2D |

Figure 2A:
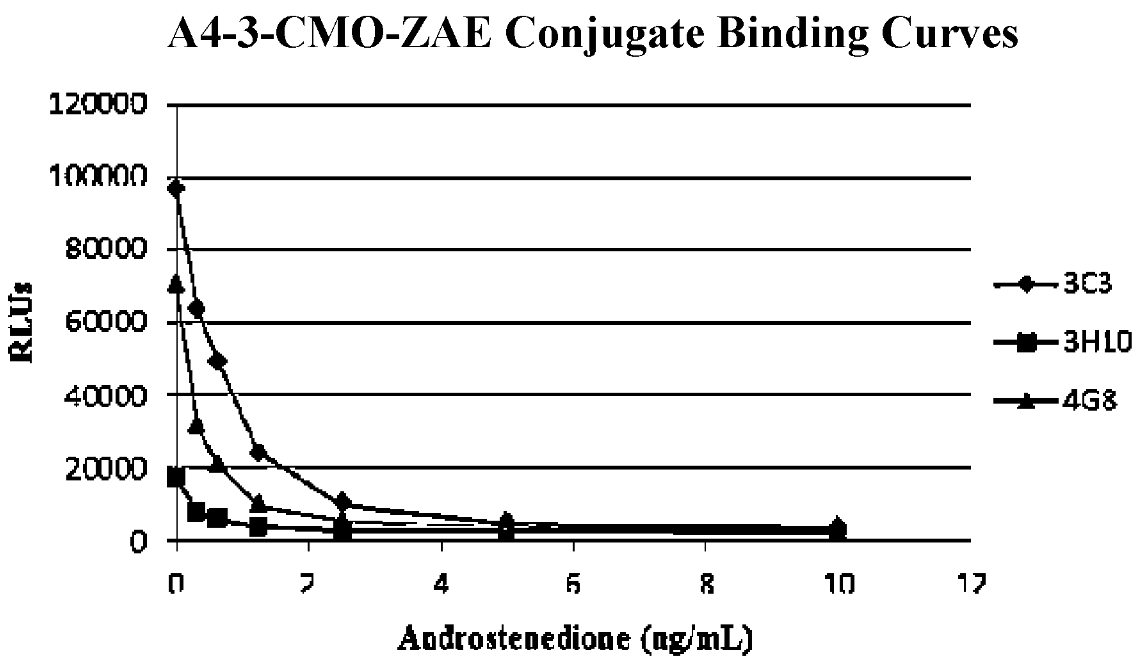
FIGS. 2A-2D each illustrate the light output of immunoassays using various A4 conjugates for 3C3, 3H10, and 4G8 antibodies which form binding complexes with 4-androstenedione.
Figure 2B:
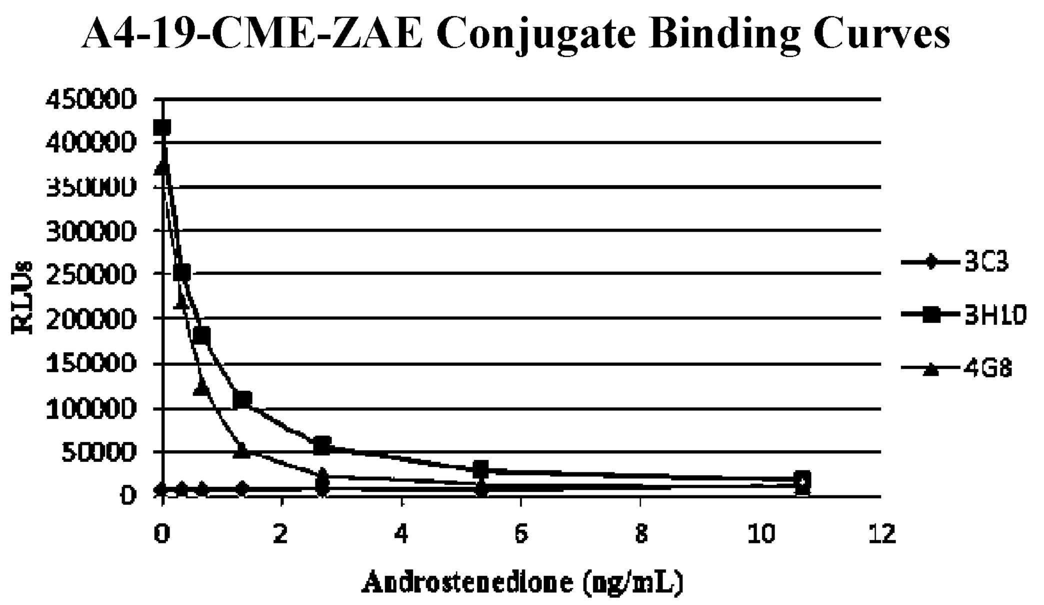
Figure 2C:
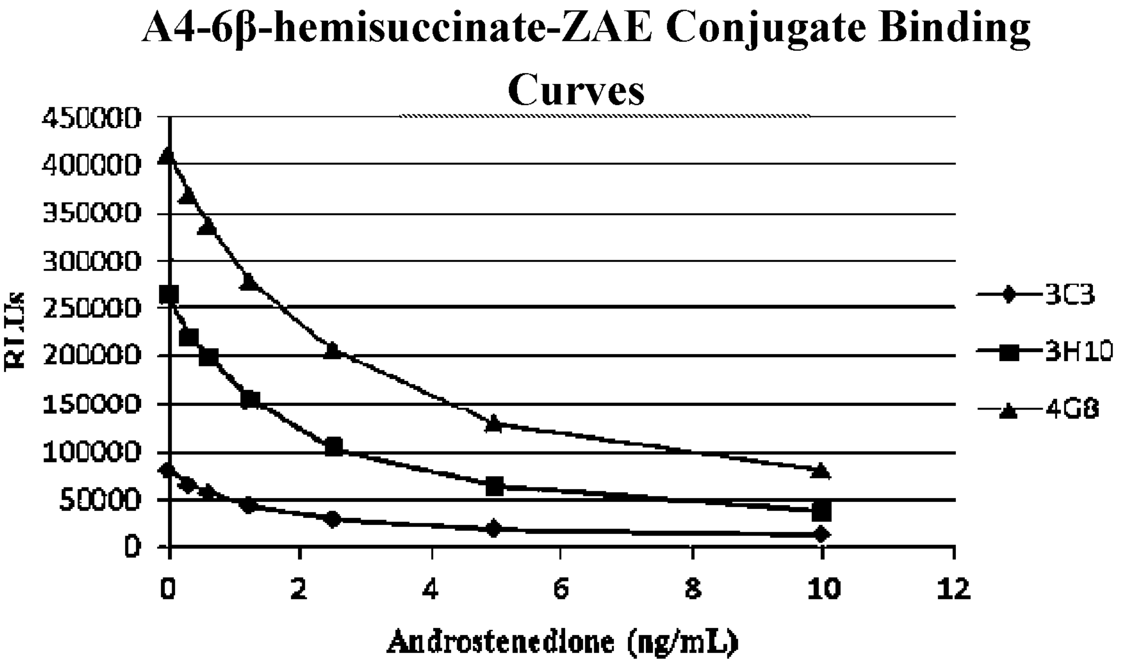
Figure 2D:
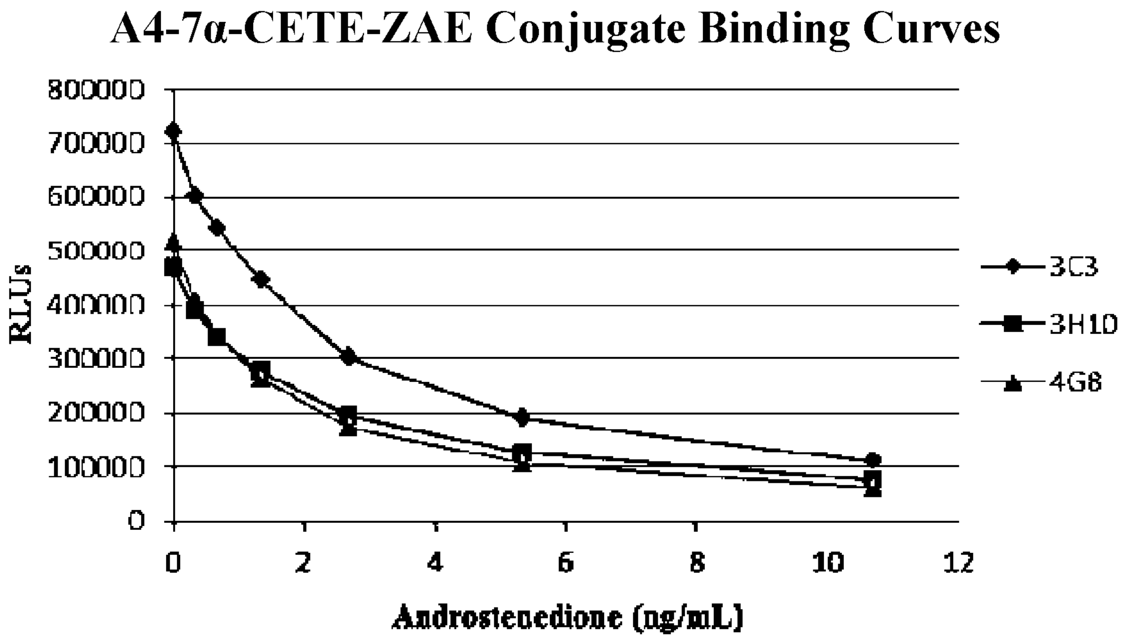

As can be seen, conjugation at the 6 or 17 positions of the androstenedione moiety ("A4-6-AE" or "A4-17-AE," respectively) with carbamate (—OC(O)NH—) linking moiety showed no appreciable binding. The A4-3-AE conjugates with a carboxy methyl oxime linking moiety ("CME," =NO—$CH_2$—C(O)—NH—) bound to the 3C3 and 3H10 antibodies, but with low affinity each antibody (as determined by signal separation and shown in FIG. 2A). Tracers with conjugation at the 19 position strongly bound to 3H10 and 4G8 antibodies without any appreciable binding to the 3C3 antibody as shown in FIG. 2B. Conjugation at the 6β or 7α positions with hemisuccinate (—OC(O)$CH_2CH_2$C(O)NH—) or carboxy ethyl thio ether ("CETE," —$SCH_2CH_2$C(O)NH—) linking moieties showed strong binding affinity for all three antibodies. Moreover, these linking moieties at these positions have different ordering of affinities for each antibody/A4-AE complex. As can be seen, the conjugate position and linking moiety of the A4-AE tracer relates to the binding affinity of that tracer to a specific antibody. For example, A4-6-AE conjugates comprising a carbamate linking moiety show no appreciable binding, while A4-6-AE conjugates comprising a hemisuccinate linking moiety show affinity for two of the three antibodies measured.

Figure 2E:
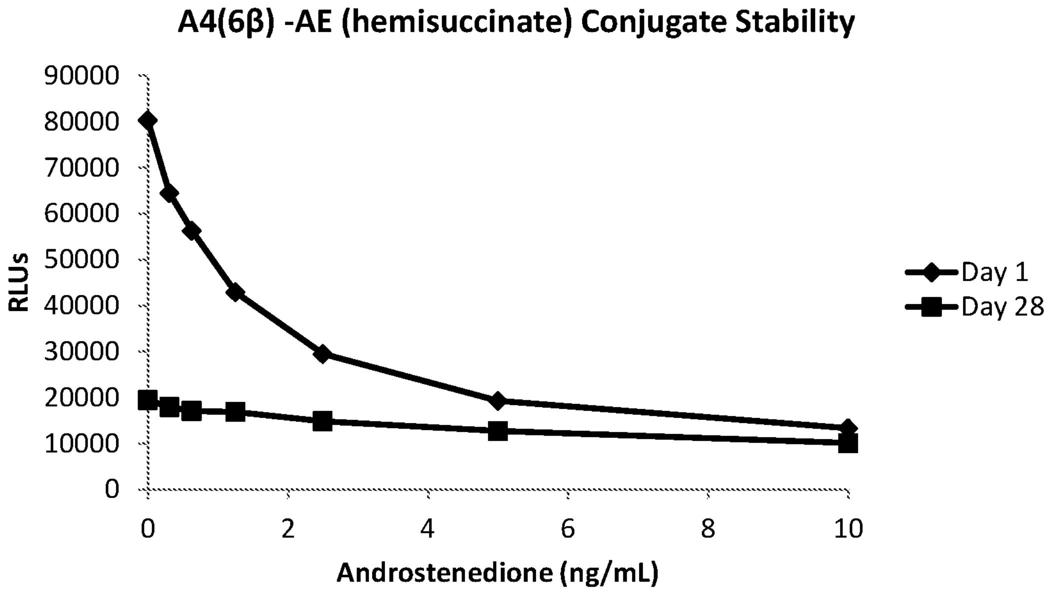
FIG. 2E shows the light output of the A4(6β)-hemisuccinate conjugate initially and 28 days after storage in a buffer solution.

The aqueous solutions of the tracers were stored at 4° C. in an aqueous buffer at pH 6.5 for 28 days and the immunoassay was rerun to determine the stability of the compounds by measurements of the change in chemiluminescence following storage. These conditions are typical for commercial automated instruments such as the ADVIA Centaur family of immunoassay analyzers. As shown in FIG. 2E, assays with A4-AE tracers comprising conjugation at the 6β position with a hemisuccinate linker showed decreased measured light output when the assay was run again at 28 days after the initial assay. As can be seen, the A4-AE tracers comprising conjugation at the 6β position show substantial loss of chemiluminescence after 28 days in the buffer system. Measurements performed on androstenedione conjugated at the 7 position (A4-7-AE) did not show a similar instability.

Example 13: Curve Shapes of A4-7-AE Conjugates

Figure 3A:
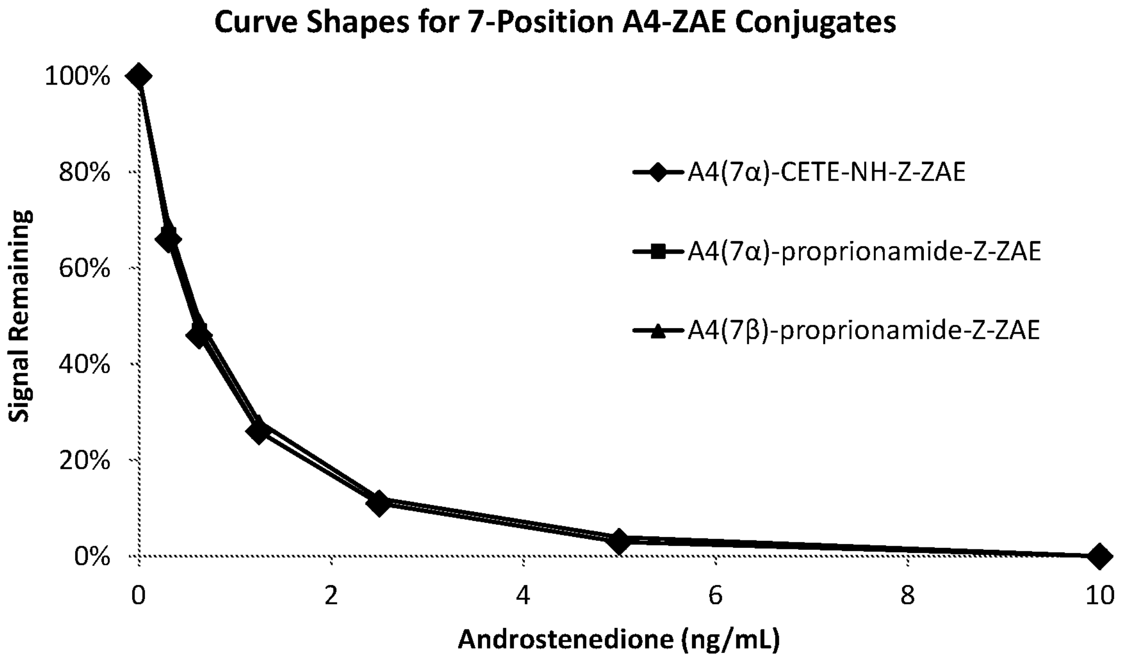
FIGS. 3A and 3B show the light output of immunoassays for samples containing various androstenedione concentrations where the immunoassay comprises A4 conjugates conjugated at the 7 position of the A4 moiety. In the immunoassays measured for FIG. 3A, the acridinium ester moiety in each conjugate is the same (-Z-NSPDMAE). In the immunoassays measured for FIG. 3B, the linkers, and acridinium ester moiety is altered.

The chemiluminescence curve shapes for several A4-7-AE conjugates were further evaluated using the 3C3 antibody. The effect of various linking moieties on the curve shape of light output as a function of androstenedione (ng/mL) was measured. Curve shapes were generated from assays using A4-AE tracers with androstenedione conjugation at the seven position with —$SCH_2CH_2$C(O)NH— or —$CH_2CH_2$C(O)NH— linking moieties. FIG. 3A illustrates the resulting signal generated by assays using three different A4-AE conjugates measured normalized as a percentage of signal generated from a lite reagent without androstenedione. In these experiments, [A4]=10 ng/mL was chosen as 0% light output. As can be seen, these A4-7-AE conjugates demonstrated equivalent curve shapes with conjugation at the 7α and 7β positions and with each of the linking moieties measured.

Figure 3B:
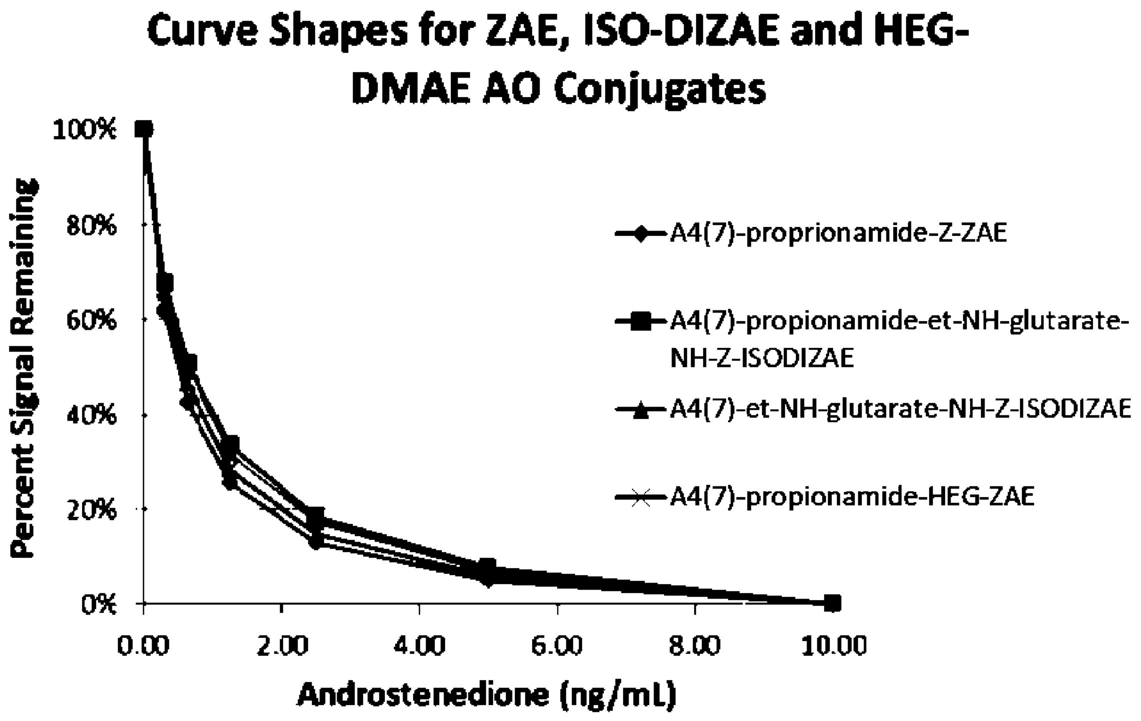

AE and/or linking moieties with various chemical properties and light outputs were also measured to determine the impact on performance in the assay. The linking moieties are conjugated to androstenedione at the 7 position. The ZAE conjugate moieties measured have the structures shown below in Table 3. Additionally, an AE moiety with a zwitterionic linker replaced by an HEG linker was also compared (HEG-ZAE). FIG. 3B shows the resulting signal generated from assays using A4-7-AE conjugates comprising the A4-AE conjugates described in Table 3.

Example 14: Non-Specific Binding of the A4-7-AE conjugates

Biotin interference in the non-specific binding of A4-7-AE conjugates was measured. An ADVIA Centaur assay with a solid phase comprising 3C3 antibody was performed on native serum comprising approximately 2.2 ng/mL androstenedione and several A4-7-AE conjugates. Biotin may disrupt the binding of the conjugates to the ANDRO solid phase by altering the surface of the streptavidin-coated beads. Accordingly, an otherwise identical assay was measured for each conjugate wherein the serum sample comprised a biotin concentration of 100 ng/mL and the results were compared to determine which conjugates are more affected by the presence of biotin during measurement. Table 4 shows the assay measured concentration of androstenedione using the samples with biotin and samples spiked with biotin. Changes in androstenedione concentration between the sample without biotin and the sample with biotin are indicative of biotin interference in the non-specific binding A4-7-AE conjugates. As can be seen, conjugates comprising a CETE linker (—$SCH_2CH_2$C(O)NH—) have greater biotin induced nonspecific binding than conjugates without the sulfur linking moiety ("carbon;" —$CH_2CH_2$C(O)NH—). This trend is seen at both the 7α and 7β conjugation configurations.

TABLE 4

| | A4-CETE-ZAE | A4-carbon-ZAE(α) | A4-carbon-ZAE(β) |
|---|---|---|---|
| Sample Without Biotin (ng/mL) | 2.17 | 2.23 | 2.22 |
| Sample with Biotin (ng/mL) | 2.33 | 2.25 | 2.23 |
| Biotin Interference (%) | 7.4% | 0.6% | 0.4% |

Example 15: Precision Measurements of A4-7-AE Conjugates

Nine serum samples comprising various androstenedione concentrations (as well as other analytes) were assayed with an ADVIA Centaur assay comprising the 3C3 antibody in order to determine the precision of A4-7-AE conjugates over a range of androstenedione concentration and testing periods. Samples included two levels of commercially available quality control materials supplied in the Liquichek® Immunoassay Plus Quality Control ("QC2" and "QC3" available from Bio-Rad, Hercules, CA). Seven other spiked native or serum patient samples were provided by Bioreclamation-IVT. Five replicate measurements of each sample were performed in a day. The five replicate measurements were also repeated over five different days. The grand mean A4 concentration (of all 25 measurements on each sample) with an A4-carbon-AE is shown in Table 5. Additionally, the ANOVA parameters standard deviation ("SD") and percent covariance ("% CV") within each five replicate measurements per day and within the average measurements over five days are shown. As can be seen, the A4-carbon-AE conjugate provides highly precise results over repeated measurements. Similar results were obtained for A4-7-ISO-DIZAE and A4-7-HEG-ZAE conjugates.

TABLE 5

| | | Within Each Day | | Over Five Days | |
|---|---|---|---|---|---|
| Sample | Mean (ng/mL) | SD | % CV | SD | % CV |
| QC2 | 1.28 | 0.037 | 2.86 | 0.037 | 2.88 |
| QC3 | 2.44 | 0.060 | 2.46 | 0.078 | 3.18 |
| 1 | 5.49 | 0.152 | 2.76 | 0.232 | 4.22 |
| 2 | 1.75 | 0.035 | 2.02 | 0.044 | 2.49 |
| 3 | 0.80 | 0.024 | 3.05 | 0.027 | 3.36 |
| 4 | 3.11 | 0.075 | 2.42 | 0.108 | 3.47 |
| 5 | 7.34 | 0.184 | 2.51 | 0.231 | 3.15 |
| 6 | 1.48 | 0.040 | 2.73 | 0.067 | 4.53 |
| 7 | 3.90 | 0.097 | 2.49 | 0.165 | 4.22 |

Example 16: Linearity Performance in an Assay Using A4-7-AE Conjugates

Seven different samples were prepared with known A4 concentrations to be analyzed with a weighted linear fit in order to determine the deviation between observed and expected androstenedione concentrations for A4-7-AE conjugates. The expected A4 concentration, the A4 concentration and the % bias to the linear model fit at each expected androstenedione concentration when using A4-carbon-AE conjugate is shown in Table 6. As can be seen, conjugation at the 7 position results in an assay with low bias from the linear model across measured androstenedione concentration ranges. Typically, the androstenedione concentration of serum derived samples will be within these ranges.

TABLE 6

| Expected [A4] (ng/mL) | Mean Assay Measured [A4] (ng/mL) | % Bias to Linear Model |
|---|---|---|
| 1.31 | 1.23 | 1.41 |
| 2.62 | 2.56 | −1.63 |
| 3.92 | 3.87 | −3.13 |
| 5.23 | 5.23 | −2.68 |

TABLE 6-continued

| Expected [A4] (ng/mL) | Mean Assay Measured [A4] (ng/mL) | % Bias to Linear Model |
|---|---|---|
| 6.54 | 6.65 | −1.63 |
| 7.85 | 8.23 | 0.99 |
| 9.16 | 9.96 | 4.43 |

Example 17: Bias of A4-7-AE Conjugates Assay Using Patient Samples

A series of patient samples obtained from BioreclamationIVT were also measured for androstenedione concentration using the ADVIA Centaur immunoassay comprising A4-carbon-AE conjugate to determine the bias of assay measurement as compared to liquid chromatographic/tandem mass spectroscopic (LC-MS/MS) measurements (ARUP Laboratories, Salt Lake City, Utah) of each sample. Patient samples were native or were spiked with additional androstenedione. Percent bias is reported as the difference between assay and LC-MS/MS measurements with respect to the LC-MS/MS measurement. Table 7 shows the results of the measurements. The A4-AE conjugates can be used to determine the concentration of androstenedione in a patient sample using an immunoassay with low bias throughout the range of androstenedione concentrations measured.

TABLE 7

| Sample | $[A4]_{LC\text{-}MS/MS}$ (ng/mL) | $[A4]_{IA}$ (ng/mL) | % Bias |
|---|---|---|---|
| 1 | 1.500 | 1.54 | 3% |
| 2 | 7.660 | 7.81 | 2% |
| 3 | 3.630 | 3.61 | −1% |
| 6 | 5.000 | 5.08 | 2% |
| 7 | 1.205 | 1.26 | 5% |
| 8 | 0.639 | 0.60 | −6% |
| 9 | 2.535 | 2.43 | −4% |

Figure 4:
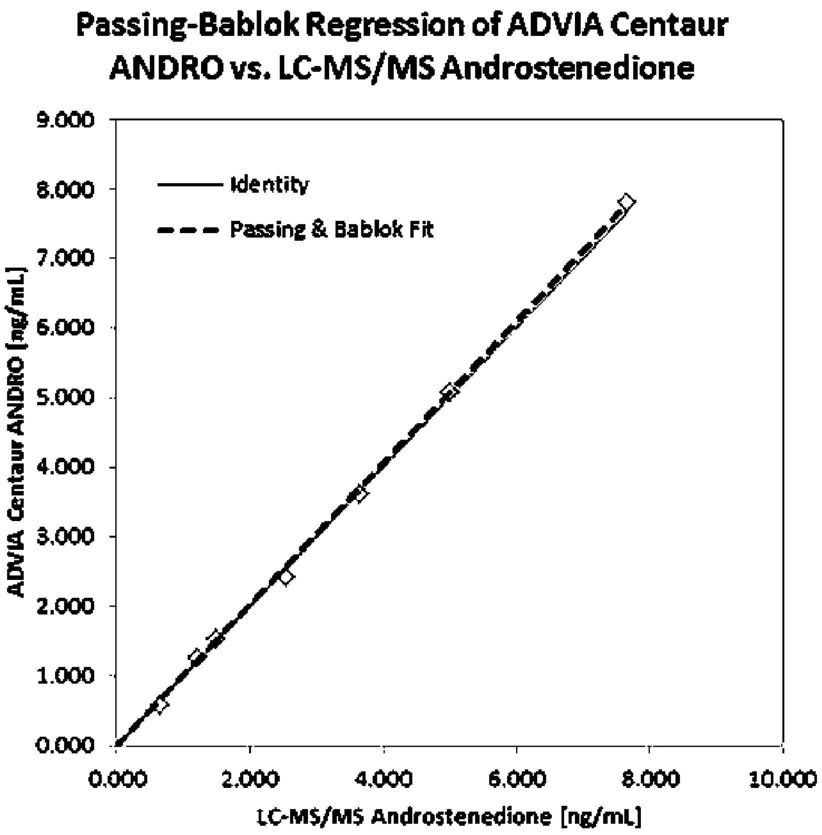
FIG. 4 shows a comparison of an LC-MS/MS assay of androstenedione samples to a competitive assay using chemiluminescent androstenedione conjugates. Results for each assay are presented in terms of the measured concentration of androstenedione. The dashed line represents the Passing-Bablok regression analysis for the data comparing each assay method (slope=1.02, intercept=−0.01).

FIG. 4 illustrates the comparison of the concentration derived from immunoassay using the A4-AE conjugate to the concentration derived from the LC-MS/MS assay. As can be seen the A4-AE conjugates are able more accurately measure the concentration of A4.

All references including patent applications and publications cited herein are incorporated herein by reference and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A detectable conjugate the structure of formula (IIIa):

(IIIa)

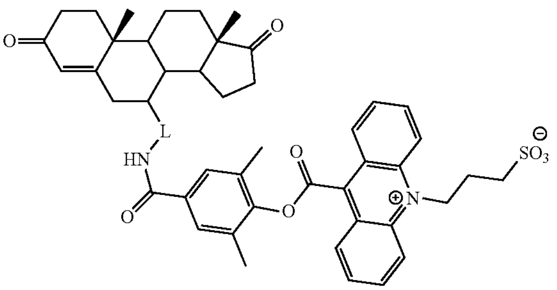

wherein L has the structure $-L^C-(Z^L)-$ $Z^L$ has the structure:

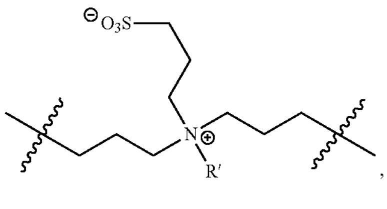

, $L^C$ has the structure:

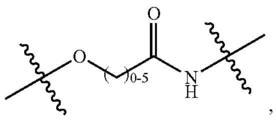

,

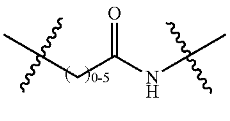

,

-continued

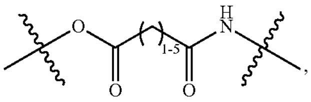

,

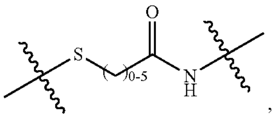

,

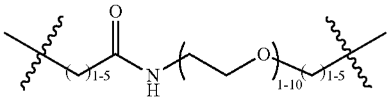

, or

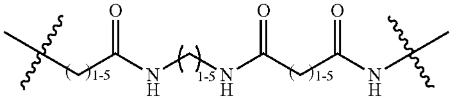

;

and

R' is independently at each occurrence hydrogen or a $C_{1-10}$ alkyl.

2. The detectable conjugate of claim 1, wherein $L^C$ is

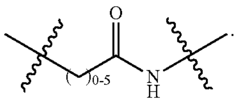

.

3. The detectable conjugate of claim 2, wherein said detectable conjugate is:

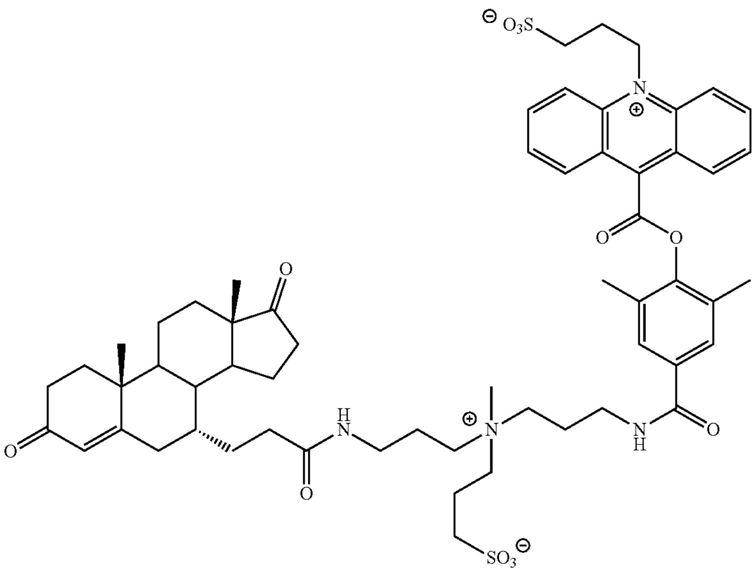

, or

-continued
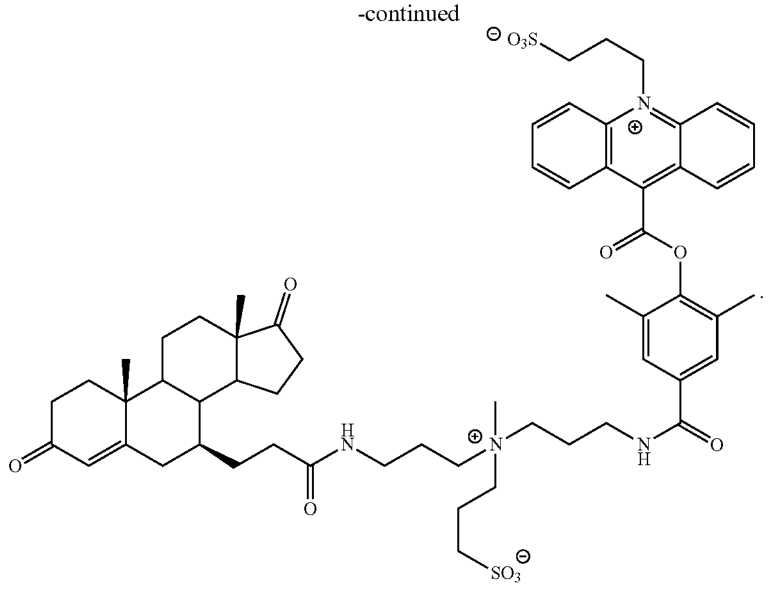
* * * * *